US005665760A

United States Patent [19]
Brown et al.

[11] Patent Number: 5,665,760
[45] Date of Patent: Sep. 9, 1997

[54] LYOPHILIZED THIOXANTHENONE ANTITUMOR AGENTS

[75] Inventors: Stephen Brown; Gurdial Singh Sandhu, both of Northumberland, England

[73] Assignee: Sanofi Winthrop, Inc., New York, N.Y.

[21] Appl. No.: 529,934

[22] Filed: Sep. 18, 1995

[51] Int. Cl.$^6$ .................................................. A01N 43/18
[52] U.S. Cl. ...................... 514/437; 514/455; 514/908; 514/970; 424/489
[58] Field of Search ............................. 514/437, 455, 514/908, 970

[56] References Cited

U.S. PATENT DOCUMENTS

| | | | |
|---|---|---|---|
| 4,582,851 | 4/1986 | Worth | 514/437 |
| 5,346,917 | 9/1994 | Miller et al. | 514/437 |

*Primary Examiner*—Frederick Krass
*Attorney, Agent, or Firm*—William J. Davis; Imre Balogh; Paul Dupont

[57] ABSTRACT

Disclosed are reconstituted lyophilized formulations for the treatment of mammalian tumors comprising a thioxanthenone antitumor agent in combination with mannitol or sucrose as a stabilizer in a lactate buffer.

10 Claims, No Drawings

LYOPHILIZED THIOXANTHENONE ANTITUMOR AGENTS

FIELD OF THE INVENTION

This invention relates to lyophilized aqueous parenteral solutions of antitumor agents. More particularly, this invention relates to lyophilized aqueous thioxanthenone antitumor agents.

Reported Developments

Many conventional drug substances and proteins destined for therapeutic or diagnostic use are unstable in aqueous solution and require conversion into solid products. For pharmaceutical products, freeze-drying is one of the most commonly used processing methods to achieve the necessary stability.

For various reasons bioactive agents are rarely freeze-dried in their pure form. Other chemical components are usually added for specific purposes, such as pH buffering, solubility enhancement or osmolarity balancing. When designing a freeze-drying process, the formulation as a whole largely governs the parameters of the cycle. Thus, any alteration in the formulation, not just the level of the active agent itself, will require further modification of a process cycle. As well as the excipients added for the above reasons, freeze-drying usually requires the incorporation of yet further additives to aid the freeze-drying process itself or to provide mechanical strength to the freeze-dried plug during subsequent storage and transport. Such excipients are referred to as lyoprotectants or stabilizers. The use of stabilizers is illustrated by the following references.

International Application No. PCT/US89/04099 (WO 90/03784) describes a lyophilized composition comprising a polypeptide and a stabilizing/ solubilizing amount of cyclodextrin selected from the group consisting of hydroxypropyl, hydroxyethyl, glucosyl, maltosyl and maltotriosyl derivatives of β- and γ-cyclodextrin.

U.S. Pat. No. 4,983,586 discloses a method for decreasing the incidence of precipitation of a lipophilic and/or water-labile drug occurring at the injection site, when the drug is being parenterally administered, comprising administering the drug in an aqueous solution containing about 20% to 50% hydroxypropyl-β-cyclodextrin. A large number of drugs are claimed including: antineoplastics, sedatives, tranquilizers, anticonvulsants, antidepressents, hypnotics, muscle relaxants, antisposmodics, anti-inflammatories, anticoagulants, cardiotonics, vasodilators and antiarrhythmics.

U.S. Pat. No. 5,298,410 discloses lyophilized formulations of biologically active substances wherein the stabilizer is a cyclodextrin derivative, a buffer such as sodium phosphate, sodium acetate and sodium carbonate. The formulations optionally may contain sucrose or trehalose.

The starting material for freeze-drying is usually an unsaturated aqueous solution, and the final product is a solid. The complete process consists of the removal of >99% of the water. During cooling, aqueous solutions become freeze-concentrated, while water is removed as ice. The whole process involves several phase transitions, e.g. liquid-solid and solid-gas, consideration of which is important for ensuring efficient processing and stable products. As the temperature is lowered, the solution will at first undercool (i.e. cool to below the equilibrium freezing temperature) before ice nucleation spontaneously occurs. Ice nucleation and crystal growth are complex processes with rates that depend on the cooling rate, solution, concentration and other factors. This stage of the process largely determines the texture of the final dried product. During freezing, the solute remains, in an increasingly concentrated form, in the residual liquid phase, the degree of concentration being governed by an equilibrium phase diagram. Eventually the solution will become saturated, at which point the solid phase of the solute will also form. The system then consists of a mixture of ice and solute crystals.

Excipients, added primarily to aid freeze-drying, usually serve one of two functions. Bulking agents are used simply to increase the total solids content, in order to achieve a mechanically more robust dried product. Such excipients must be made to crystallize from solution during the freeze-drying process, preferably during the freezing stage, as it is only as a separate phase that they will have a neutral effect on product stability. Stabilizers, on the other hand, afford chemical protection during freeze-concentration and aid in the formation of the glassy state; they also provide physical strength to the dried plug. The glass transition temperature is a function of the chemical composition of the total solid material.

While the physico-chemical basis for correct formulation of products for freeze-drying has received considerable attention in the prior art (see, for example, Franks, F. Freeze-drying: a combination of physics, chemistry, engineering and economics, Jap. J. Freeze Drying, 38, 5–16 (1992)), the physico-chemical basis is insufficient to enable one skilled in the art to produce the end products which satisfy the desired objectives. Painstaking research and/or surprising discovery is still the real basis by which proper products can be produced as will become clear as the description of the present invention proceeds.

We have now discovered by doing painstaking research that thioxanthenone antitumor compounds, which when delivered in customary pharmaceutical vehicles such as tablets and capsules for oral administration, would not quite satisfy the requirements of an effective product, could be made into lyophilized pharmaceutical formulations which, upon reconstitution, becomes injectable. The lyophilized formulations were found stable without degradation/ alteration during extended shelf life.

SUMMARY OF THE INVENTION

In accordance with the present invention, there are provided reconstituted lyophilized formulations for the treatment of mammalian tumors comprising:

a) of from about 1 to about 50 mg/ml and preferably of from about 10 to 20 mg/ml of a thioxanthenone antitumor agent defined hereinafter;

b) of from about 10 mg/ml to about 125 mg/ml and preferably of from about 30 mg/ml to 100 mg/ml of a stabilizer selected from the group consisting of mannitol and sucrose; and c) of from about 0.025 to about 0.25M of a lactate buffer and preferably sodium lactate buffer, said formulation having a pH of from about 3.0 to about 4.5.

Preferred formulations of the present invention contain the antitumor agent N-[[1-[[2-(di-methylamino)ethyl] amino]-9-oxothioxanthene-4-yl]methyl]-methanesulfonamide and sucrose as the stabilizing agent.

The reconstituted lyophilized formulations of the present invention are administered to mammals for the treatment of tumors.

DETAILED DESCRIPTION OF THE INVENTION

The lyophilized formulation of the present invention comprises: a thioxanthenone antitumor agent; and an aqueous vehicle.

The antitumor agents

The antitumor agents of the present invention have the formula (I) according to U.S. Pat. No. 5,346,917 which is incorporated herein by reference in its entirety:

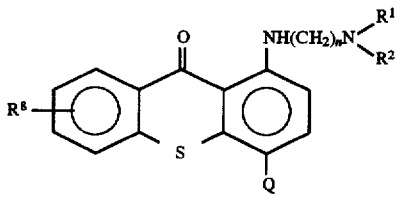

I wherein n is 2 or 3;

$R^1$ and $R^2$ are independently lower-alkyl;

Q is a residue chosen from the group consisting of $CH_2NHR^3$, $CH_2N(R^4)SO_2R^7$, $CH_2NHCHO$, $CH=N$—Ar, $C(O)NR_5R^6$, $CH_2N(R^4)C(O)R^7$, $CH_2N(C_2H_5)$ CHO, $CH_2N$ $(R^4)$ $P(O)$ $(O$-lower-alkyl$)_2$, $CH_2N=CH$—N $(R^9)(R^{10})$, $CH_2N(R^4)C(O)CF_3$ and $CH_2N(R^4)C(O)OR^7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy;

Ar is phenyl or phenyl substituted with methyl, methoxyl, hydroxy, halogen or nitro, with the proviso that when n is 2, $R^1$ and $R^2$ are ethyl, $R^8$ is hydrogen and Q is $CH_2NHSO_2Ar$, the Ar group cannot be 4-monosubstituted by methyl or halogen; and $R^9$ and $R^{10}$ are independently lower-alkyl; or a pharmaceutically acceptable acid-addition salt or solvate thereof. The compounds are useful for the treatment of tumors in mammals.

Preferred antitumor agents are represented in the formula (II):

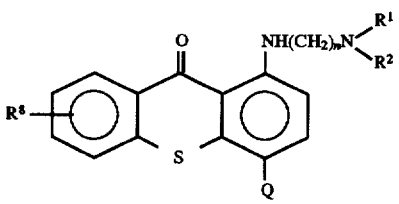

II wherein n is 2 or 3;

$R^1$ and $R^2$ are independently lower-alkyl;

Q is a residue chosen from the group consisting of $CH_2NHR^3$, $CH_2NHCHO$, $CH=N$—Ar, $C(O)NR^5R^6$, $CH_2N$ $(R^4)$ $C(O)$ $R^7$, $CH_2N$ $(C_2H_5)$ CHO, $CH_2N$ $(R^4)$ $P(O)(O$-lower-alkyl$)_2$, $CH_2N=CH$—$N(R^9)$ $(R^{10})$, $CH_2N$ $(R^4)C(O)$ $CF_3$ and $CH_2N$ $(R^4)C(O)$ $OR^7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy; Ar is phenyl or phenyl substituted with methyl, methoxyl, hydroxy, halogen or nitro, and $R^9$ and $R^{10}$ are independently lower-alkyl; or a pharmaceutically acceptable acid-addition salt or solvate thereof.

Representative compounds are shown in the following examples:

EXAMPLE 1

1-[[2-(Diethylamino)ethyl]amino]-4-(N-phenylformimidoyl)thioxanthen-9-one (I: $R^1=R^2=Et$; Q=CH=N—$C_6H_5$; $R^8=H$; n=2)

A mixture of 17.7 g (50 mmol) of 1-[[2-(diethylamino)ethyl]amino]-9-oxo-thioxanthen-4-carboxyaldehyde and 15.1 g (150 mmol) of aniline in 100 mL of toluene was refluxed for 8 hours with a Dean-Stark trap. TLC on alumina with chloroform/hexane/- isopropylamine 10:10:2 indicated incomplete reaction. The toluene was distilled off, 25 mL of aniline was added and the mixture refluxed for 4 hours. Fifty mL of xylene was added and the reaction refluxed again for 3 hours. The solvent and excess aniline were removed in vacuo and the residue recrystallized from benzene to yield 19.9 g of crude product. This was recrystallized from approximately 1.5L hexane to yield 15.8 g (86%) of product, m.p. 125°–126°.

EXAMPLE 2

N-[[1-[[2-(Diethylamino)ethyl]amino]-9-oxothioxanthen-4-yl]methyl]formamide (I: $R^1=R^2=Et$; Q=$CH_2NHCHO$; $R^8=H$; n=2)

A solution of 35.4 g (0.1 mol) of 1-[[2-(diethylamino)-ethyl]amino]-9-oxo-thioxanthen-4-carboxyaldehyde, 420 mL of formamide and 50 mL (1 mol) of formic acid was heated at 160° for 1 hour. The reaction was cooled, poured into 2L of water and made basic with about 50 mL of 35% sodium hydroxide solution. The gummy precipitate was filtered off and dried in vacuo. The dried precipitate was dissolved in about 1.5L of hot ethyl acetate, treated with charcoal, and crystallized by cooling. The product was filtered off, washed with ethyl acetate and dried to provide 29.0 g (75%) of product, m.p. 154°–155°.

EXAMPLE 3

N-[[1-[[2-(Diethylamino)ethyl]amino]-9-oxothioxanthen-4-yl]methyl]-N-methylformamide (IV: $R^1=R^2=Et$; $R^4=Me$; $R^8=H$; n=2)

By a procedure analogous to that of Example 2, 24.6 g of the N-methylformamide was prepared from 35.4 g (0.1 mol) of 1-[[2-(diethylamino)ethyl]amino]-9-oxo-thioxanthen-4-carboxyaldehyde, 394 g of N-methylformamide and 50 mL of formic acid. The product was recrystallized from 150 mL of acetone to a m.p. of 127°–130°.

EXAMPLE 4

4-(Aminomethyl)-1-[[2-(diethylamino)ethyl]amino]-thioxanthen-9-one (I: $R^1=R^2=Et$; Q=$CH_2NH_2$; $R^8=H$; n=2)

A solution of 24.4 g (64 mmol) of the formamide of Example 2 in 240 mL of 2N hydrochloric acid was heated on a steam bath for 1 hour. The reaction was cooled to room temperature, made basic with 35% aqueous sodium hydroxide, and the resulting yellow precipitate collected by filtration. The product was dissolved in benzene, treated with charcoal, dried with magnesium sulfate, filtered and azeotroped to remove traces of water. The dried residue was crystallized from methanol and isopropanol by the addition of ethereal hydrogen chloride. The resulting solid was recrystallized in several crops from methanol to yield 10.6 g of product, m.p. 270°–272°, as the dihydrochloride salt.

EXAMPLE 5

1-[[2-(Diethylamino)ethyl]amino]-4-[(methylamino)-methyl]thioxanthen-9-one (I: $R^1=R^2=Et$; $Q=CH_2NHCH_3$; $R^8=H$; n=2)

By a process precisely analogous to that of Example 4, 10.5 g of the methylamine was obtained as the dihydrochloride hemihydrate from 14.6 g (37 mmol) of the N-methylformamide of Example 3 and 150 mL of 2N hydrochloric acid. The product melted at 241°–243°.

EXAMPLE 6

N-[[1-[[2-(Diethylamino)ethyl]amino]-9-oxothioxanthen4-yl]methyl]methanesulfonamide (I: $R^1=R^2=Et$; $Q=CH_2NHSO_2CH_3$; $R^8=H$; n=2)

A solution of 10.65 g (30 mmol) of the free base of the amine of Example 4 in 100 mL of pyridine was cooled in an ice bath and 4 g (35 mmol) of methanesulfonylchloride was added in one portion. The mixture was stirred for 2 hours at room temperature and poured into 750 mL of water containing 2 g of sodium hydroxide. The dark yellow precipitate was collected, washed with water and dried in vacuo overnight. A second crop was obtained by adding excess sodium hydroxide to the filtrate and filtering the resulting solid. The combined precipitates after drying were recrystallized from benzene to yield 6.4 g of the methanesulfonamide, m.p. 169°–170°.

EXAMPLE 7

1-[[2'-(Diethylamino)ethyl]amino]-9-oxothioxanthene-4-carboxamide (I: $R^1=R^2=Et$; $Q=CONH_2$; $R^8=H$; n=2)

A suspension of 74 g (0.23 mol) of 1-[[2-(diethylamino)-ethyl]amino]-9-oxo-thioxanthen-4-carboxaldehyde and 74 g (1.06 mol) of hydroxylamine hydrochloride in 400 mL of pyridine and 400 mL of ethanol was refluxed 0.5 hour and 70 mL of water was added to provide a homogeneous solution. The solution was heated for a further 2 hours and allowed to sit at room temperature 14 hours. The resulting crystalline oxime was filtered off to provide a quantitative yield, mp 215°–218°.

One hundred twenty-three grams of the oxime was heated briefly on a steambath in 180 mL of acetic anhydride to achieve solution. The solution was cooled, 100 mL of 1.8 M HCl in ether was added and the resulting suspension was diluted with 500 mL of ether. The suspension was allowed to sit 14 hours at 0° and filtered. The residue (123 g, mp 109°–112°) was slurried in 250 mL of xylene and refluxed 20 min. The mixture was cooled and 71.3 g of the nitrile was filtered off, mp 265°.

Ten grams of the nitrile was stirred in 200 mL of conc. $H_2SO_4$ at room temperature for 3 days. The reaction was neutralized with conc. $NH_4OH$ and the residue filtered off. The residue was digested in warm EtOAc/EtOH, filtered and the product crystallized from the chilled solution, mp 241°–243°. It was dissolved in ethanol and one equivalent of HCl in ethanol was added. Six grams of the amide hydrochloride was obtained, mp 271°–272°.

EXAMPLE 8

N-[[1-[[2-(Diethylamino)ethyl]amino]-9-oxothioxanthen-yl]methyl]N-methylmethanesulfonamide (I: $R^1=R^2=Et$; $Q=CH_2N(CH_3)SO_2CH_3$; $R^8=H$; n=2)

A solution of 1.5 g (3.5 mmol) of the methanesulfonamide of Example 6 in THF (60 mL) was cooled to O_C in an ice-bath and NaH 0.16 g (4.0 mmol) was added. The reaction mixture was warmed to room temperature, stirred for 10 minutes, then methyl iodide 0.25 mL (4.0 mmol) was added. The reaction mixture was stirred at room temperature for 24 hours and the solvent was removed in vacuo. The residue was purified by column chromatography on silica eluting with chloroform (100%) then 1% isopropylamine/chloroform to afford 1.15 g (74%) of the N-methylmethanesulfonamide as a yellow powder, m.p. 175°–177° C. The free base was also treated with methanesulfonic acid in methanol to afford the methanesulfonate salt, m.p. 194°–195.5° C. (labelled Example 8a hereinafter).

EXAMPLE 9

N-[[1-[[2-(Diethylamino)ethyl]amino]-9-oxothioxanthen-4-yl]methyl]phenylsulfonamide (I: $R^1=R^2=Et$; $Q=CH_2NHSO_2Ph$; $R^8=H$; n=2)

Following a procedure substantially similar to that described in Example 6, 2.4 g (57%) of the phenylsulfonamide was obtained as the methanesulfonic acid salt from 2.54 g (7.15 mmol) of the free base of the amine of Example 4, pyridine (50 mL) and benzenesulfonyl chloride (1.1 mL, 8.62 mmol), followed by treatment with methanesulfonic acid in methanol. The product was recrystallized from ethanol.

EXAMPLE 10

N-[[1-[[2-(Diethylamino)ethyl]amino]-9-oxo-thioxanthen-4-yl]methyl]acetamide (I: $R^1=R^2=Et$; $Q=CH_2NHC(O)CH_3$; $R^8=H$; n=2)

Following a procedure substantially similar to that described in Example 6, 2.3 g (52%) of the acetamide was obtained as an orange solid from 4.15 g (11.7 mmol) of the free base of the amine of Example 4, pyridine (60 mL) and acetyl chloride (0.82 mL, 11.53 mmol). The product was recrystallized from acetone and melted at 182°–183° C.

EXAMPLE 11

N-[[1-[[2-(Diethylamino)ethyl]amino]-9-oxothioxanthen-4-yl]methyl]benzamide (I: $R^1=R^2=Et$; $Q=CH_2NHC(O)Ph$; $R^8=H$; n=2)

Following a procedure substantially similar to that described in Example 6, 1.02 g (68%) of the benzamide was obtained as a yellow powder from 1.17 g (3.29 mmol) of the free base of the amine of Example 4, pyridine (25 mL) and benzoyl chloride (0.42 mL, 3.62 mmol). The product was purified by column chromatography on silica eluting with chloroform (100%) to 1% isopropylamine/chloroform, followed by recrystallization from ethyl acetate. The product melted at 161°–163° C.

EXAMPLE 12

N-[[1-[[2-(Diethylamino)ethyl]amino]-9-oxothioxanthen-4-yl]diethyl phosphoramide (I: $R^1=R^2=Et$; $Q=CH_2NHP(O)(OEt)_2$; $R^8=H$; n=2)

A solution of 2.28 g (6.41 mmol) of the free base of the amine of Example 4, $CH_2Cl_2$ (50 mL), and triethylamine (2 mL) at 0° C. was treated with diethyl phosphorochloridate (1.0 mL, 6.9 mmol). The reaction mixture was stirred at 0° C. for 2 hours, then at room temperature for 1 hour. The solvent was removed in vacuo and the residue was purified by column chromatography on silica eluting with ethyl acetate (100%), then 5% methanol/ethyl acetate and finally methanol/isopropylamine/ethyl acetate (5/5/90) to afford 2.28 g (72%) of the diethyl phosphoramide as a yellow solid, m.p. 108°–110° C. when recrystallized from ethyl acetate.

EXAMPLE 13

N-[[1-[[2-(Diethylamino)ethyl]amino]-9-oxothioxanthen-4-yl]methyl]-N-ethylformamide (IV: $R^1=R^2=Et$; $R^4=Et$; $R^8=H$; n=2)

A solution of 2.0 g (5.6 mmol) of 1-[[2-(diethylamino)ethyl]amino]-9-oxo-thioxanthen-4-carboxaldehyde, N-ethylformamide (24.0 mL) and formic acid (3.0 mL, 79.5 mmol) was heated at 170° C. for 4 hours. The reaction mixture was cooled, poured into water and made basic with 10% sodium hydroxide. A solid was obtained which was collected by filtration and washed with water. The solid residue was taken up in chloroform/water, and the organic layer was separated and dried over $Na_2SO_4$. The solvent was removed in vacuo and the residue was purified by radial chromatography eluting with isopropylamine/methanol/ethyl acetate (0.5/1/98.5) to afford 1.32 g (57%) of the N-ethylformamide as an orange solid, m.p. 75°–77° C.

EXAMPLE 14

1-[[2-(Diethylamino)ethyl]amino]-4-[(ethylamino)methyl]thioxanthen-9-one (I: $R^1=R^2=Et$; $Q=CH_2NHC_2H_5$; $R^8=H$; n=2)

By a process substantially similar to that described in Example 4, 1.29 g (92%) of the ethylamine was obtained as the dihydrochloride from 1.3 g (3.2 mmol) of the N-ethylformamide of Example 13 and 10.8 mL of 2N hydrochloric acid. The product was recrystallized from ethanol/ tetrahydrofuran and melted at 160° C. (dec.).

EXAMPLE 15

1-[[2-(Diethylamino)]ethyl]amino]-4-(dimethylaminomethylene-aminomethyl)-thioxanthen-9-one trihydrochloride (I: $R^1=R^2=Et$; $Q=CH_2N=CHN(Me)_2$; $R^8=H$; n=2)

N-[[1-[[2-(Diethylamino)]ethyl]amino]-9-oxothioxanthen-4-yl]methyl]formamide (3 g) was diluted with 50 mL of 2N HCl and the solution was heated on a steam bath for 90 min. The mixture was cooled, basified to pH 10 with 35% sodium hydroxide solution, and extracted into chloroform. The organic layer was separated, filtered through $K_2CO_3$, and concentrated in vacuo and the resulting crude product was allowed to react with dimethylformamide dimethylacetal overnight at 60° C. Excess DMF-dimethyl acetal was removed in vacuo and the desired title compound was purified by flash chromatography (silica gel; chloroform/iPrNH$_2$/MeOH (98:1:1). This product was dissolved in 2.5 M HCl/EtOH (100 mL), cooled in an ice-bath, filtered, and dried to afford 2.38 g of 1-[[2-(diethylamino)]ethyl]amino]-4-(dimethylaminomethyleneaminomethyl)-thioxanthen-9-one trihydrochloride as a orange solid, m.p. 258°–260° C.

EXAMPLE 16

N-[[1-[[2-(Diethylamino)ethyl]amino]-9-oxothioxanthen-4-yl]methyl]-trifluoroacetamide (I: $R^1=R^2=Et$; $Q=CH_2NHC(O)CF_3$; $R^8=H$; n=2)

A solution of 4-(aminomethyl)-1-[[2-(diethylamino)ethyl]-amino]thioxanthen-9-one (2.91 g; 8.19 mmol) in 80 mL of methylene chloride at 0° C. was treated with trifluoroacetyl chloride (14.75 mL of 0.61M solution in toluene; 9.0 mmol) and the reaction mixture was stirred at 0° C. for 90 min. The mixture was concentrated in vacuo and the residue was purified by flash chromatography (silica gel; EtOAc (100%), then 2% isopropylamine/EtOAc) and then recrystallization from ethyl acetate to afford 2.52 g (68%) of the product as the free base, m.p. 189°–190° C. (Example 16). The free base was dissolved in methanol and treated with methanesulfonic acid (0.55 g, 5.72 mmol) to afford the methanesulfonate salt, m.p. 152°–154° C. after recrystallization from acetone (Example 16a).

EXAMPLE 17

(a)

A mixture of thiosolicyclic acid (50.14 g. 0.33 mol) and cupric acetate (5.0 g) in DMSO (500 mL) was brought to reflux and potassium carbonate (54.3 g) was added in portion. 3-Bromochlorobenzene (42 mL, 0.36 mol) was then added via syringe and the mixture was refluxed for 3 hours. The reaction mixture was poured into water, treated with charcoal and filtered through celite. The filtrate was acidified with concentrated HCl and the precipitate which formed was collected by filtration, washed with water and dried in vacuo at 60° C. to afford 75.01 g (85%) of 2-[(3-chlorophenyl)thio]benzoic acid.

(b)

To a stirred solution of concentrated $H_2SO_4$ at 0° C. was added 2-[(3-chlorophenyl)thio)benzoic acid (75.00 g, 0.28 mol) in portions over 1 hour. The mixture was stirred for 2 hours, poured into concentrated $NH_4OH$ (500 mL) in water (2.5 L) and the precipitate which formed was collected by filtration, washed with water and dried in vacuo at 60° C. to afford 65.9 g (95%) of a mixture of 1-chloro and 3-chlorothioxanthen-9-One.

(c)

A mixture of 1-chloro and 3-chlorothioxanthen-9-one (14.01 g, 56.8 mmol), pyridine (20 mL) and diethylaminopropylamine (5.13 g, 39.4 mmol) was refluxed until the reaction was complete. The heat was removed, the solvent was removed in vacuo and the residue was taken up in chloroform and purified by column chromatography on silica eluting with chloroform to remove the unreacted 3-chloroisomer and then 5% isopropylamino/chloroform to afford 5.10 g (54%) of 1-[[3-(diethylamino)propyl]amino]-thioxanthen-9-one as an orange gum.

(d)

A mixture of 1-[[3-(diethylamino)propyl]amino]-thioxanthen-9-one (5.10 g, 15.0 mmol), formalin (160 mL) and 5N acetic acid (0.8 mL) was heated to 90° C. 16 hours, additional 5N acetic acid (0.20 mL) was added, followed by formalin (50 mL) and the mixture was heated at 90° C. for approximately 57 hours. The mixture was diluted with water, basified with 5N NaOH and extracted with chloroform. The organic layer was dried over $Na_2SO_4$ and passed through a silica column eluting with 2% methanol/chloroform and then isopropylamine/methanol/chloroform (2/2/96) to afford 3.82 g (69%) of 1-[[3-(diethylamino)propyl]amino]-4-(hydroxymethyl)-thioxanthen-9-one as an orange/brown gum.

(e)

1-[[3-(Diethylamino)propyl]amino]-9-oxothioxanthen-4-carboxaldehyde (II: $R^1=R^2=Et$; $R^8=H$; n=3)

A mixture of 1-[[3-(Diethylamino)propyl]amino]-4-(hydroxymethyl)-thioxanthen-9-one (3.82 g), toluene (60 mL) and manganese oxide (7.5 g) was refluxed for 6.5 hours. The mixture was cooled to room temperature, filtered through celite, and the filtrate was concentrated in vacuo to afford 3.3 g (87%) of 1-[[3-(Diethylamino)propyl]amino]-9-oxothioxanthen-4-carboxaldehyde as a brown oil.

(f)

1-[[3-(Diethylamino)propyl]amino]-4-(methylaminomethyl)thioxanthen-9-one dihydrochloride 3/2 hydrate (I: $R^1=R^2=Et$; Q=$CH_2NHMe$; $R^8=H$; n=3)

A solution of 1-[[3-(diethylamino)propyl]amino]-9-oxothioxanthen-4-carboxaldehyde (3.3 g, 8.96 mmol) and 3 g of formic acid in 50 mL of N-methylformamide was allowed to reflux for 2 h. The mixture was basified with 5 mL of a 5N sodium hydroxide solution and extracted into chloroform (3×150ml). The organic layer was dried over sodium sulfate, concentrated in vacuo, and a crude oil was dissolved in a 3N aqueous HCl solution (50 ml) and heated on a steam bath for 3 h. The above mixture was cooled, basified with 30 mL of 35% NaOH, extracted into chloroform (3×150 ml), the organic layer dried over sodium sulfate and concentrated in vacuo to afford a brown oil. The brown oil was purified by flash chromatography (silica gel; 5% triethylamine/$Et_2O$ then 5% $Et_3N$/EtOAc, then triethylamine/methanol/EtOAc (5:5:90)) to afford 1.1 g of 1-[[3-(diethylamino)-propyl]amino]-4-(methylaminomethyl)thioxanthen-9-one, as a clear orange gum. The above gum was converted into the corresponding dihydrochloride by treatment with 6N HCl in ether to afford 1.04 g of the dihydrochloride·3/2 hydrate as a yellow powder, m.p. 222°–224° C.

EXAMPLE 18

(a)

4-(Aminomethyl)-1-[[2-(dimethylamino)ethyl]amino]-9-oxothioxanthen-9-one dihydrochloride·½ hydrate (I: $R^1=R^2=Me$; Q=$CH_2NH_2$; $R^8=H$; n=2)

A mixture of N-[[1-[[2-(dimethylamino)ethyl]amino]-9-oxothioxanthen-4-yl]methyl]formamide (6.2 g) and 2N HCl (52 mL) was heated to 100° C. for 1.5–2 hours. The reaction mixture was poured into ice water, basified with 35% NaOH, and extracted with chloroform. The organic layer was washed with water (2X), then brine (1X), dried over $Na_2SO_4$ and concentrated in vacuo. The residue was purified by column chromatography on silica eluting with ethyl acetate, then 0.5% triethylamine/EtOAc, then 2% triethylamine/EtOAc, then $CHCl_3$/1–2% isopropylamine and finally $CHCl_3$/1–2% isopropylamine/2% MeOH to afford 3.3 g (58%) of the product as the free base. A portion of the free base (1.25 g) was dissolved in methanol and treated with concentrated HCl (3.3 mL) in MeOH (6 mL) to afford 1.2 g of the product as the dihydrochloride·½ hydrate, m.p. 213° C. (dec.).

(b)

N-[[1-[[2-(Dimethylamino)ethyl]amino]-9-oxothioxanthen-4-yl]methyl]methanesulfonamide methanesulfonate (I: $R^1=R^2=Me$; Q=$CH_2NHSO_2Me$; $R^8=H$; n=2)

4-(Aminomethyl)-1-[[2-(dimethylamino)]ethyl]amino]-thioxanthen-9-one (2 g, 6 mmol) in 30 mL of dry pyridine under nitrogen was stirred at room temperature until the solution was complete. The solution was chilled in an ice-bath and 0.52 mL (6.7 mmol) of methanesulfonyl chloride in chilled pyridine was added dropwise and the mixture was stirred for 1 h at room temperature. The reaction mixture was poured into 500 mL of water containing 0.51 g of sodium hydroxide, extracted into chloroform, the organic layer was washed with water (2x) and brine, and dried over anhydrous sodium sulfate. The mixture was filtered and concentrated in vacuo. The residue (2.5 g) was stirred in ether, filtered, and dried to afford 2 g of N-[[1-[[2-(dimethylamino)ethyl]amino]-9-oxothioxanthen-4-yl]methyl]methane-sulfonamide, m.p. 126°–127° C. The free base was dissolved in MeOH, and treated with methanesulfonic acid (0.48 g) to afford 2.0 g (67%) of the product as the methanesulfonate salt, m.p. 168° C. (dec.).

(c)

A mixture of 1-[[2-(dimethylamino)ethyl]amino]-4-(hydroxymethyl)-thioxanthen-9-one (9.2 g, 0.028 mol) in toluene (322 mL) was heated to about 60° C. and then manganese oxide ($MnO_2$, 16 g) was added and the mixture was heated at 60° C. for 1 hour. The mixture was filtered and the filtrate was concentrated in vacuo to afford 7.9 g (87%) of 1-[[2-(dimethylamino)-ethyl]amino]-9-oxothioxanthen-4-carboxaldehyde (Formula II: $R^1=R^2=Me$; $R^8=H$; n=2).

(d)

N-[[1-[[2-(Dimethylamino)ethyl]amino]-9-oxothioxanthen-4-yl]methyl]formamide (I: $R^1=R^2=Me$; Q=$CH_2NHCHO$; $R^8=H$; n=2)

A mixture of 1-[[2-(dimethylamino)ethyl]amino]-9-oxothioxanthen-4-carboxaldehyde (4.75 g), formamide (66.5 mL) and formic acid (7.6 mL) was heated at 170° C. for 4 hours. The mixture was poured into ice water (250 mL), basified with 35% NaOH and extracted with chloroform. The organic layer was washed with water (2X), then brine (1X) and the solvent was dried over $Na_2SO_4$ and concentrated in vacuo to afford 6.3 g of N-[[1-[[2-(dimethylamino)ethyl]amino]-9-oxothioxanthen-4-yl]methyl]formamide.

(e)

4-(Aminomethyl)-1-[[2-dimethylamino)ethyl]amino] -9-oxothioxanthen-9-one dihydrochloride·½ hydrate (I:$R^1$=$R^2$=Me; Q=$CH_2NH_2$; $R^8$=H; n=2 )

A mixture of N-[[1-[[2-(dimethylamino)ethyl]amino]-9-oxothioxanthen-4-yl]methyl]formamide (6.2 g) and 2N HCl (52 mL) was heated to 100° C. for 1.5–2 hours. The reaction mixture was poured into ice water, basified with 35% NaOH, and extracted with chloroform. The organic layer was washed with water (2x), then brine (1x), dried over $Na_2SO_4$ and concentrated in vacuo. The residue was purified by column chromatography on silica eluting with ethyl acetate, then 0.5% triethylamine/EtOAc, then 2% triethylamine/EtOAc, then $CHCl_3$/1–2% isopropylamine and finally $CHCl_3$/1–2% isopropylamine/2% MeOH to afford 3.3 g (58%) of the product as the free base. A portion of the free base (1.25 g) was dissolved in methanol and treated with concentrated HCl (3.3 mL) in MeOH (6mL) to afford 1.2 g of the product as the dihydrochloride·½ hydrate, m.p. 213° C. (dec.).

(f)

N-[[1-[[2-(Dimethylamino)ethyl]amino]-9-oxothioxanthen-4-yl]methyl]methanesulfonamide methanesulfonate (I: $R^1$=$R^2$=Me; Q=$CH_2NHSO_2Me$; $R^8$=H; n=2)

4-(Aminomethyl)-1-[[2-(dimethylamino)ethyl]amino]-thioxanthen-9-one (2 g, 6 mmol) in 30 mL of dry pyridine under nitrogen was stirred at room temperature until the solution was complete. The solution was chilled in an ice-bath and 0.52 mL (6.7 mmol) of methanesulfonyl chloride in chilled pyridine was added dropwise and the mixture was stirred for 1 h at room temperature. The reaction mixture was poured into 500 mL of water containing 0.51 g of sodium hydroxide, extracted into chloroform, the organic layer was washed with water (2x) and brine, and dried over anhydrous sodium sulfate. The mixture was filtered and concentrated in vacuo. The residue (2.5 g) was stirred in either, filtered, and dried to afford 2 g of N-[[1-[[2-(dimethylamino)ethyl]amino]-9-oxothioxanthen-4-yl]methyl]methane-sulfonamide, m.p. 126°–127° C. The free base was dissolved in MeOH and treated with methane sulfonic acid (0.48 g) to afford 2.0 g (67%) of the product as the methanesulfonate salt, m.p. 168° C. (dec.).

EXAMPLE 19

(a)

Following a procedure similar to that described in Example 17(c), there was prepared 6.83 g of 1-[[3-(dimethylamino)propyl]amino]thioxanthen-9-one, from a mixture of 1-chloro and 3-chlorothioxanthen-9-one (15.15 g, 61.4 mmol), pyridine (20 mL) and dimethylaminopropylamine (6.01 g, 58.7 mmol).

(b)

Following a procedure similar to that described in Example 17(d), there was obtained 6.74 g (90%) of 1-[[3-(dimethylamino)propyl]amino]-4-(hydroxymethyl) thioxanthen-9-one, from 1-[[3-(dimethylamino)propyl] amino]-thioxanthen-9-one (6.8 g, 21.8 mmol), formalin (175 mL) and glacial acetic acid (0.75 mL).

(c)

Following a procedure similar to that described in Example 17(e), there was obtained 4.2 g of 1-[[3-(dimethylamino)propyl]amino]-9-oxothioxanthen-4-carboxaldehyde (Formula II: : $R^1$=$R^2$=Me; R=H; n=3) from 1-[[3-(dimethylamino)propyl]amino]-4-(hydroxymethyl)thioxanthen-9-one (6.7 g), toluene (80 mL) and $MnO_2$ (12.15 g). The product was purified by column chromatography on silica eluting with $CHCl_3$ (1.00%) to 1% isopropylamine/$CHCl_3$.

(d)

A mixture of N-methylformamide (50 mL), formic acid (5.2 g) and 1-[[3-(dimethylamine) propyl]amino]-9-oxothioxanthen-4-carboxaldehyde (4.14 g, 12.16 mmol) was refluxed for 3 hours. The mixture was diluted with water (250 mL), basified with 35% NaOH and extracted with $CHCl_3$ (3×150 mL) . The organic layer was dried over $Na_2SO_4$, passed through a plug of silica eluting with $CHCl_3$ (100%), then 2% isopropylamine/$CHCl_3$ to afford 3.93 g (84%) of N-[[1-[[3-(dimethylamino)-propyl]amino]-9-oxothioxanthen-4-yl]methyl]-N-methylformamide (Formula IV: : $R^1$=$R^2$=Me; $R^4$=Me; $R^5$=H; n=3).

(e)

1- [[3- (Dimethylamino)propyl]amino]-4-[(methylaminomethyl]thioxanthen-9-one dihydrochloride monohydrate ($R^1$=$R^2$=Me; Q=$CH_2NHMe$; $R^8$=H; n=3)

A solution of the above N-methylformamide (3.83 g; 10 mmol) in 40 mL of 3N HCl was heated on a steam bath for 4 h; neutralized with 35% NaOH solution, and chilled on ice for 1 h. The liquid layer was decanted and a crude product was dissolved in chloroform and filtered through silica gel (chloroform; 1% isopropylamine/chloroform) to afford 2.38 g of the desired amine as an orange gum. The product was converted into the corresponding hydrochloride salt by dissolution in MeOH and treatment with concentrated HCl to afford 0.98 g of the dihydrochloride monohydrate, m.p. 228°–229° C.

(a)

A mixture of 1-[[2-(dimethylamino)ethyl]amino]-9-oxothio-xanthen-4-carboxaldehyde (4.75 g, 0.15 mol), N-methylformamide (48 mL) and formic acid (3.9 mL) was heated at 170° C. for 4.5 hours and then was allowed to stand at room temperature for approximately 64 hours. The reaction mixture was poured into water (250 mL), basified with 35% NaOH, extracted with $CHCl_3$ (3x), the organic layer was separated, washed with water (2x) and then brine (1x) and was dried over $Na_2SO_4$. The solvent was removed in vacuo to afford 5.75 g of N-[[1-[[2-(dimethylamino)ethyl] amino]-9-oxothioxanthen-4-yl]methyl]-N-methyl formamide [Formula IV: $R^1$=$R^2$=Me; $R^4$=Me; $R^8$=H; n=3)

(b)

1-[[2-(Dimethylamino)ethyl]amino]-4-[ (methylamino)-methyl]thioxanthen-9-one dihydrochloride-¾ hydrate (I: $R^1$=$R^2$=Me; Q=$CH_2NHMe$; $R^8$=H; n=2)

By a process similar to that of Example 19E, 1.8 g of 1-[[2-(dimethylamino)ethyl]amino]-4-[(methylamino)

methyl]thioxanthen-9-one was obtained from 5.7 g (15.4 mmol) of the corresponding N-methylformamide of Example 20(a) and 50 mL of 2 N HCl. after purification of the free base by flash chromatography (silica gel; chloroform; then 0.5% isopropylamine/ chloroform; then 1% isopropylamine/chloroform). The free base was converted into the corresponding dihydrochloride 5/4 hydrate salt by treating with conc. HCl in methanol to afford 1.8 g (30%) of the product, m.p. 177° C. (dec.).

EXAMPLE 21

(a)

A solution of [[3-(dimethylamino)propyl]amino]-9-oxothioxanthen-4-carboxaldehyde (3.6 g; 10.57 mmol) in 50 mL of formamide containing 3.6 g of formic acid was refluxed for 1.5 h and then was allowed to stand at room temperature overnight. the reaction mixture was diluted with water (400 mL), basified with 3 mL of 5N NaOH solution, stirred rapidly for 30 min, and the precipitated solid was filtered, washed with water, and dried, yielding 3.1 g (79%) of N-[[1-[[3-(dimethylamino)propyl]amino]-9-oxothioxanthen-4-yl]methyl]-N-methyl formamide (Formula I: $R^1=R^2=Me$; $Q=CH_2NHCHO$; $R^8=H$; n=3), as a yellow powder.

(b)

A solution of the formamide of Example 21(a)(2.98 g; 8.07 mmol) in 40 mL of 3N HCl was heated on a steam bath for 4 h, allowed to cool to room temperature, chilled on ice, and neutralized to pH 8 with 5 N NaoH solution. the resulting heterogeneous mixture was extracted into chloroform (5×100 mL) and the organic layer was dried over sodium sulfate and filtered through a pad of silica gel (first 5% triethylamine/ether, then 1–5% isopropylamine/chloroform) to afford 2.3 g (83%) of 4-(aminomethyl)-1-[[3-(dimethylamino) propyl]amino]thioxanthen-9-one (Formula I: $R^1=R^2=Me$; $Q=CH_2N\ H_2$; $R_8=H$; n=3).

(c)

N-[[1-[[3-(Dimethylamino)propyl]amino]-9-oxothioxanthen-4-yl]methyl]methanesulfonamide methanesulfonate-½ hydrate (I: $R^1=R^2=Me$; $Q=CH_2NHSO_2Me$; $R^8=H$; n=3)

To an ice cold solution of the amine of Example 21(b) (2.2 g; 6.44 mmol) in pyridine was added methanesulfonyl chloride (0.51 ml; 6.59 mmol) and the resulting mixture was stirred at room temperature overnight. The mixture was diluted with chloroform and passed through a large plug of silica gel eluting with 5% triethylamine/EtOAc affording 1.32 g of N-[[1-[[3-(dimethylamino)propyl]amino]-9-oxothioxanthen-4-yl]methyl]-methanesulfonamide as a yellow powder. The free base was dissolved in methanol (10 mL) and treated with methanesulfonic acid (0.31 g, 1 eq.) in methanol to afford 1.38 g of the methanesulfonate-1/2 hydrate salt as an orange solid, m.p. >107° C.

EXAMPLE 22

N-[[1-[[2-(Diethylamino)ethyl]amino]-9-oxothioxanthen-4-yl]methyl]-N-methyl-ethanesulfonamide methanesulfonate (I: $R^1=R^2=Et$; $Q=CH_2N(CH_3)SO_2Et$; $R^8=H$; n=2)

A solution of 2.03 g (5.49 mmol) of 1-[[2-(diethylamino) ethyl]amino]-4-[(methylamino)methyl]thioxanthen-9-one (prepared by the method described in Example 5) and triethylamine in 45 mL of methylene chloride was cooled to 0° C. and treated with ethanesulfonyl chloride (0.74 g, 5.76 mmol). After 15 min at 0° C., the reaction mixture was stirred at room temperature for 72 h. The mixture was concentrated in vacuo, the residue dissolved in chloroform and purified by passing through a pad of silica gel (chloroform; then 1% triethylamine/chloroform) affording 2.43 g (96%) of N-[[1-[[2-(diethylamino)ethyl]amino]-9-oxothioxanthen-4-yl]methyl]-N-methylethanesulfonamide. The sulfonamide was recrystallized from ethyl acetate and treated with methanesulfonic acid in isopropanol to afford the product as the methanesulfonate salt, m.p. 159°–161° C.

EXAMPLE 23

N-[[1-[[2-(Diethylamino)ethyl]amino]-9-oxothioxanthen-4-yl]methyl](p-methoxy)benzenesulfonamide methanesulfonate (I: $R^1=R^2=Et$; $Q=CH_2NHSO_2C_6H_4$-p-OMe; $R^8=H$; n=2)

A solution of 1.40 g (3.94 mmol) of 4-(aminomethyl)-1-[[2-(diethylamino)ethyl]amino]-thioxanthen-9-one (prepared by the method described in Example 4) in 30 mL of chloroform containing 1.5 mL of triethylamine was cooled to 0° C. and treated with p-methoxybenzenesulfonyl chloride (0.83 g, 4.02 mmol). After 10 min at 0° C. the reaction mixture was stirred at room temperature for 2 h. Chloroform was removed in vacuo, the residue dissolved in 100 mL of methylene chloride containing 1 mL of triethylamine and treated with additional p-methoxybenzenesulfonyl chloride (0.85 g) with stirring at room temperature. The mixture was concentrated in vacuo, the residue was purified by passing through a pad of silica gel (1% triethylamine/chloroform) affording 1.57 g of N-[[1-[[2-(diethylamino)ethyl]amino]-9-oxothioxanthen-4-yl]methyl]-p-methoxy-benzenesulfonamide. The sulfonamide was treated with methanesulfonic acid (0.3 g) in isopropanol/isopropyl acetate/methanol to afford 1.07 g of the methanesulfonate salt, m.p. 133°–137° C.

EXAMPLE 24

N-[[1-[[2-(Diethylamino)ethyl]amino]-9-oxothioxanthen-4-yl]methyl]ethanesulfonamide methanesulfonate (I: $R^1=R^2=Et$; $Q=CH_2NHSO_2Et$; $R^8=H$; n=2)

A solution of 2.5 g of 4-(aminomethyl)-1-[[2-(diethylamino) ethyl]amino]-thioxanthen-9-one (prepared by the method described in Example 4) in 30 mL of pyridine was cooled in an ice bath for 15 min and 0.95 g of ethanesulfonyl chloride in 5 mL of pyridine was added rapidly dropwise and the reaction mixture was stirred at room temperature for 1 h. The mixture was poured into 75 mL of water containing 0.75 g of NaOH, extracted into chloroform, the organic layer was washed with water (2x) and brine, and dried over sodium sulfate. The mixture was concentrated in vacuo and the residue was stirred in ether and dried (40° C./0.1 mm) to afford 1.7 g of N-[[1-[[2-(diethylamino)ethyl]amino]-9-oxothioxanthen-4-yl]methyl]ethane-sulfonamide, m.p. 105° C. (dec.). The sulfonamide was dissolved in methanol and treated with methanesulfonic acid in methanol to afford 1.61 g (42%) of the methanesulfonate salt, m.p. 135° C. (dec.).

EXAMPLE 25

N-[[1-[[2-(Diethylamino)ethyl]amino]-9-oxothioxanthen-4-yl]methyl]-N-ethyl-methanesulfonamide (I: R¹=R²=Et; Q=CH₂N(Et) SO₂Me; R⁸=H; n=2)

A solution of 2.10 g (5.48 mmol) of 1-[[2-(diethylamino) ethyl]amino]-4-[(ethylamino)methyl]thioxanthen-9-one (prepared by the method of Example 14) in 30 mL of methylene chloride was cooled to 0° C. and treated with 2 mL of triethylamine and methanesulfonyl chloride (0.7 ml) and the reaction mixture was stirred at room temperature for 6 h. The solvent was removed in vacuo, the residue dissolved in chloroform, and the solution was purified by passing through a pad of silica gel (eluting with chloroform followed by 2% triethylamine/chloroform). The yellow solid isolated was recrystallized from ethyl acetate and dried to afford 1.11 g (44%) of N-[[1-[[2-(diethylamino)ethyl] amino]-9-oxothixanthen-4-yl]methyl]-N-ethylmethanesulfonamide as a yellow powder, m.p. 172°–176° C.

EXAMPLE 26

N-[[1-[[2-(Diethylamino)ethyl]amino]-9-oxothioxanthen-4-yl]methyl]-3,4-dichlorobenzenesulfonamide methanesulfonate·1/2 hydrate (I: R¹=R²=Et; Q=CH₂NHSO₂C₆H₃-3,4-dichloro; R⁸=H; n=2)

To a solution of 3,4-dichlorobenzenesulfonyl chloride (1.84 g, 7.5 mmol) in 35 mL of dry pyridine was added 2.5 g (7 mmol) of 4-(aminomethyl)-1-[[2-(diethylamino)ethyl] amino]-thioxanthen-9-one (prepared by the method described in Example 4) under nitrogen and the reaction mixture was stirred at room temperature for 15 min. and then was allowed to stand for approximately 72 hours. The reaction mixture was poured into 75 mL of water containing 0.75 g of NaOH, and extracted into chloroform. The organic layer was washed with water (2x) and brine, and dried over sodium sulfate. Chloroform was removed in vacuo, the residue was recrystallized from ethanol to afford 1.24 g of N-[[1-[[2-(diethylamino)]ethyl]amino]-9-oxothioxanthen-4-yl]methyl]-3,4-dichlorobenzenesulfonamide, m.p. 95° C. (dec.). The free base was dissolved in methanol and treated with methanesulfonic acid in methanol to afford the methanesulfonate·1/2 hydrate, m.p. 55° C. (dec.).

EXAMPLE 27

N-[[1-[[2-(Diethylamino)ethyl]amino]-9-oxothioxanthen-4-yl]methyl]-2-fluorobenzenesulfonamide (I: R¹=R²=Et; Q=CH₂NHSO₂C₆H₄-2-F; R⁸=H; n=2)

A solution of 1.36 g (3.83 mmol) of 4-(aminomethyl)-1-[[2-(diethylamino)ethyl]amino]-thioxanthen-9-one (prepared by the method described in Example 4) in 25 mL of methylene chloride containing 1 mL of triethylamine was cooled to 0° C. and treated with 2-fluorobenzenesulfonyl chloride (0.84 g; 4.32 mmol) and the reaction mixture was stirred for several hours. The solvent was removed in vacuo, the residue dissolved in chloroform, and purified by flash chromatography (silica gel: chloroform followed by 1% triethylamine/chloroform). The solvent was removed in vacuo and the product was recrystallized from ethyl acetate affording 1.08 g (55%) of N-[[1-[[2-(diethylamino)ethyl] amino]-9-oxothioxanthen-4-yl]methyl]-2-fluorobenzenesulfonamide as an orange powder, m.p. 125°–127° C.

EXAMPLE 28

N-[[1-[[2-(Diethylamino)ethyl]amino]-9-oxothioxanthen-4-yl]methyl]-N-propyl-methanesulfonamide (I: R¹=R²=Et; Q=CH₂N(C₃H₇)SO₂Me; R⁸=H; n=2)

The oil from 0.2 g of 60% dispersion of sodium hydride in mineral oil was removed by triturating with pentane (4x). Dry DMF (40 ml) was added under nitrogen to sodium hydride with stirring, and 2 g of N-[[1-[[2-(diethylamino) ethyl]amino]-9-oxothioxanthen-4-yl]methyl] methanesulfonamide (Example 6) was then added to the reaction mixture while stirring under nitrogen and the mixture was heated to 50° C. for 2 h. The above mixture was chilled in an ice bath for 15 min, 0.87 g of propyl iodide in a small volume of DMF was added, and the mixture was allowed to stir at room temperature overnight. The mixture was stirred with 35 mL of water, filtered, and the residue was washed with water and dried (50° C./0.1 mm/P205) to afford 2.17 g of N-[[1-[[2-(diethylamino)ethyl]amino]-9-oxothioxanthen-4-yl]methyl]-N-propylmethanesulfonamide, m.p. 142°–143° C.

EXAMPLE 29

N-[[1-[[2-(Diethylamino)ethyl]amino]-9-oxothioxanthen-4-yl]methyl]-N-methyl-benzenesulfonamide methanesulfonate (I: R¹=R²=Et; Q=CH₂N(Me)SO₂C₆H₅; R⁸=H; n=2)

A solution of 5.32 g (14.4 mmol) of 1-[[2-(diethylamino) ethyl]amino]-4-[(methylamino)methyl]thioxanthen-9-one (prepared by the method described in Example 5) in 100 mL of methylene chloride was cooled to 0° C. and treated with triethylamine (5 mL) and benzenesulfonyl chloride (2 mL; 15.67 mmol) and the reaction mixture was stirred for 2 h. The mixture was concentrated in vacuo, and the residue was purified by passing through a pad of silica gel (eluting with chloroform; then ½%–1% isopropylamine/chloroform) yielding 6.24 g of a yellow gum. The product was dissolved in ethyl acetate and the solvent removed in vacuo affording 6.06 g (83%) of N-[[1-[[2-(diethylamino)ethyl]amino]-9-oxothioxanthen-4-yl]methyl]-N-methylbenzenesulfonamide. The sulfonamide (2.5 g) was suspended in isopropanol and treated with methanesulfonic acid (0.51 g) to yield 2.63 g of the methanesulfonate salt, m.p. 171°–174° C.

EXAMPLE 30

(a)

To a mixture of m-anisic acid (250 g, 1.67 mol) in acetic acid (1 L) was added bromine (85 mL) and then water (1L). The mixture was heated to reflux, cooled in an ice bath and the product which precipitated was collected by filtration and washed with water to afford 305.7 g (79%) of 2-bromo-5-methoxybenzoic acid, m.p. 154°–156° C.

(b)

To a mixture of 3-chlorothiophenol (20 g, 138 mol), and cupric acetate (1.8 g) and DMF (200 mL) was added K₂CO₃ (23 g). The mixture was heated to 150° C. for 15–20 minutes, then 2-bromo-5-methoxybenzoic acid (35.8 g, 0.155 mol) was added in portions. The mixture was heated overnight, poured into water (600 mL), filtered and the filtrate was treated with charcoal, filtered and diluted with HCl. The resulting precipitate was collected by filtration, washed with water, and dried at 50° C. in vacuo over $P_2O_5$ to afford 27.6 g of 2-[(3-chlorophenyl)thio]-5-methoxybenzoic acid.

(c)

To cooled sulfuric acid (89 mL) under nitrogen was added 2-[(3-chlorophenyl)thio-5-methoxybenzoic acid (27 g, 0.092 mol) in portions over 1.5–2 hours. The mixture was stirred at ambient temperature overnight, poured into water (900 mL) containing conc. $NH_4OH$ (218 mL) and ice. The solid which precipitated was collected by filtration and dried at 50° C. in vacuo over $P_2O_5$ to afford 21 g (42%) of a mixture of 1-chloro and 3-chloro-7-methoxy-thioxanthen-9-one.

(d)

A mixture of 1-chloro and 3-chloro-7-methoxy-thioxanthen-9-one (20.7 g), pyridine (69 mL) and diethylaminoethylamine (16.1 g, 0.138 mol) was heated at 115° C. under $N_2$ for 20 hours. The solvent was removed in vacuo and the residue was purified by column chromatography on silica eluting with $CHCl_3$ (100%) and then 1% isopropylamine/chloroform to afford 11.22 g of 1-[[2-(diethylamino)ethyl]amino]-7-methoxythioxanthen-9-one.

(e)

a mixture of 1-[[2-(diethylamino)ethyl]amino]-7-methoxythioxanthen-9-one (11.2 g, 0.031 mol), 37% formaldehyde (277 mL) and 5N acetic acid (4.6 mL) was heated at 100° C. for 3 hours, the reaction mixture was cooled, filtered, and the filtrate was poured into ice-water (600 mL) and made basic with 35% NaOH. The mixture was extracted with chloroform (3x), washed with brine and dried over $Na_2SO_4$. The solvent was removed in vacuo and the residue was purified by column chromatography on silica eluting with 25% $CHCl_3$/hexane, then 50% CHCl3/hexane, then 75% CHCl3/hexane, then 0.5% isopropylamine/CHCl3 to afford 8.8 g (73%) of 1-[[2-(diethylamino)-ethyl]amino]-4-(hydroxymethyl)-7-methoxythioxanthen-9-one.

(f)

A solution of 1-[[2-(diethylamino)ethyl]amino]-4-(hydroxymethyl)-7-methoxythioxanthen-9-one (8.8 g, 0.023 mol) in toluene (268 mL) was heated to 60° C. under nitrogen and then $MnO_2$ (13.2 g) was added. The mixture was heated overnight, filtered, and the filtrate was concentrated in vacuo to afford 7.05 g (81%) of 1-[[2-(diethylamino)ethyl]amino]-7-methoxy-9-oxothioxanthen-4-carboxaldehyde (Formula II: $R^1=R^2=Et$; $R^8=7-OCH_3$; n=2).

(g)

A solution of 1-[[2-(diethylamino)ethyl]amino]-7-methoxy-9-oxothioxanthen-4-carboxaldehyde (3 g, 7.8 mmol) and 1.5 mL of formic acid in 25.5 mL of N-methylformamide was heated to 170° C. for 8 h with stirring under nitrogen. The reaction mixture was poured into 160 mL of ice/water, basified with 35% of NaOH solution, and extracted into chloroform (3x). the organic layer was washed with water (2x) and brine, dried over sodium sulfate, and the sovlent was removed in vacuo affording 3 g (89.9%) of the desired N-[[1-[[2-(diethylamino)ethyl]amino]-7-methoxy-9-oxothioxanthen-4-yl]methyl]-N-methylformamide (Formula IV: $R^1=R^2=Et$; $R^4=Me$; $R^8=7-OCH_3$; n=2).

(h)

1-[[2-(Diethylamino)ethyl]amino]-4-[(methylamino)methyl]-7-methoxy-thioxanthen-9-one (I: $R^1=R^2=Et$; $Q=CH_2NHMe$; $R^8=7-OMe$; n=2)

The N-methylformamide of Example 30(g) (3.0 g) in a 2N aqueous HCl solution (24 mL) was heated at 100° C. for 2 h under nitrogen with stirring. The above mixture was cooled, poured into 125 mL of ice/water, basified with 35% NaOH solution, and was extracted into chloroform and washed with water (2X), then brine. The organic layer was dried over sodium sulfate and concentrated in vacuo to afford 3.1 g of the crude product. The product was triturated in ether and the filtrate was purified by several flash chromatography columns (silica gel; eluting with 50% hexane/chloroform, then chloroform, and then 0.25–0.5% isopropylamine/chloroform (column 1); chloroform, then 1% isopropylamine/1% $MeOH/CHCl_3$ (column 2); and $CHCl_3$, then 0.5% isopropylamine/$CHCl_3$ (column 3)) affording 0.746 g of 1-[[2-(diethylamino)ethyl]amino]-4-[(methylamino]methyl]-7-methoxy-thioxanthen-9-one.

EXAMPLE 31

(a)

N-[[1-[[2-(Diethylamino)ethyl]amino]-7-methoxy-9-oxothioxanthen-4-yl]methyl]-N-methylformamide (I: $R^1=R^2=Et$; $Q=CH_2NHCHO$; $R^8=7-OMe$; n=2)

A mixture of 1-[[2-(diethylamino)ethyl]amino]-7-methoxy-9-oxothioxanthen-4-carboxaldehyde (3.6 g, 0.0094 mol), formamide (48 mL) and formic acid (6 mL) was heated to 170° C. under $N_2$ for 8 hours. The mixture was poured into ice-water, basified with 35% NaOH and extracted with chloroform. The organic layer was separated, washed with water (2x), then brine and was dried over $Na_2SO_4$ and concentrated in vacuo to afford 3.88 g of N-[[1-[[2-(diethylamino)ethyl]amino]-7-methoxy-9-oxothioxanthen-4-yl]methyl]-N-methylformamide.

(b)

4-(Aminomethyl)-1-[[2-(diethylamino)ethyl]amino]-7-methoxy-thioxanthen-9-One (I: $R^1=R^2=Et$; $Q=CH_2NH_2$; $R^8=7-OCH_3$; n=2)

A mixture of the formamide of Example 31(a) (3.88 g) and 2N NCl (32 mL) was heated at 100° C. for 2 h under nitrogen with stirring. The above mixture was cooled, poured into water, basified with 10% NaOH solution, and extracted into chloroform and washed with water, then brine. The organic layer dried over sodium sulfate and concentrated in vacuo to afford 3.6 g of the crude product. The product was dissolved in chloroform and purified by flash chromatography (silica gel; eluting with hexane/chloroform (50:50) and then 1% isopropylamine in hexane/chloroform (50:50)) affording 1.75 g of the desired product.

(c)

N-[[1-[[2-(Diethylamino)]ethyl]amino]-7-methoxy-9-oxothio-xanthen-4-yl]methyl]-methanesulfonamide (I: $R^1=R^2=Et$; $Q=CH_2NHSO_2Me$; $R^8=7-OMe$; n=2)

To a solution of 1.75 g (0.0045 mol) of the amine of Example 31(b) in 22.5 mL of pyridine cooled in an ice bath under nitrogen with stirring was added dropwise 0.39 mL (0.005 mol) of methanesulfonyl chloride in a small volume of pyridine and the resulting reaction mixture was stirred at room temperature for 2 h. The mixture was poured into 375 mL of water containing 0.38 g of NaOH, extracted into chloroform, and the organic layer was washed with water and brine. The chloroform layer was dried over sodium sulfate, the solvent removed in vacuo, and the residue was dried in vacuo to afford 1.61 g (77%) of N-[[1-[[2-(diethylamino)ethyl]amino]-7-methoxy-9-oxothioxanthen-4-yl]methyl]methanesulfonamide, m.p. 144° C. (dec.).

EXAMPLE 32

(a)

To a mixture of 3-chlorothiophenol (20 g, 0.138 mol), cupric acetate (1.75 g) and DMF (199 mL) under $N_2$ was added in portions $K_2CO_3$ (23 g). The mixture was heated to 150° C. and then 2,5-dibromobenzoic acid (43.5 g) was added. The mixture was heated overnight, poured into water (600 mL), filtered, the filtrate was treated with charcoal and filtered again. The filtrate was acidified with conc. HCl, extracted with $CHCl_3$, the organic layer was washed with brine and dried over $Na_2SO_4$. The solvent was removed in vacuo to afford 28.9 g of 2-[(3-chlorophenyl)thio]-5-bromobenzoic acid.

(b)

A mixture of 2-[(3-chlorophenyl)thio]-5-bromobenzoic acid (28.4 g) and conc. sulfuric acid (80 mL) was stirred at 0° C. and then at room temperature overnight. The mixture was poured into ice-water (850 mL) containing conc. $NH_4OH$ (199 mL) and the product which precipitated was collected by filtration and dried at 50° C. in vacuo to afford 15.0 g of a mixture of 1-chloro and 3-chloro-7-bromo-thioxanthen-9-one.

(c)

A mixture of 1-chloro and 3-chloro-7-bromothioxanthen-9-one (13.6 g), pyridine (108 mL) and N,N-diethylethylene diamine (16.3 mL) was heated to 115° C. for 20 hours. The solvent was removed in vacuo, and the residue was purified by column chromatography on silica eluting with $CHCl_3$ (100%), then 1% isopropylamine/$CHCl_3$ to afford 9.3 g of 1-[[2-(diethylamino)ethyl]amino]-7-bromothioxanthen-9-one.

(d)

A mixture of 1-[[2-(diethylamino)ethyl]amino]-7-bromothioxanthen-9-one (9.3 g, 22.9 mmol), 203 mL of 37% formaldehyde solution, and 3.4 mL of 5N acetic acid solution was heated to 100° C. under nitrogen overnight. The mixture was cooled to room temperature and the solid formed was removed by filtration. The filtrate was diluted with water, basified with 35% NaOH solution and extracted into chloroform. The organic layer was washed with brine, dried over sodium sulfate, and the solvent was removed in vacuo to afford 10 g of oil. The above oil in methylene chloride was filtered, the solvent concentrated in vacuo, and the crude hydroxymethyl analog was purified by flash chromatography (silica gel; eluting with 25% chloroform/hexane, then chloroform/hexane (1:1), then 25% chloroform/hexane, then $CHCl_3$ (100%), and then 0.5–1% isopropylamine/chloroform) to afford 3.2 g of 1-[[2-(diethylamino)ethyl]amino]-4-(hydroxymethyl)-7-bromothioxanthen-9-one.

(e)

1-[[2-(Diethylamino)ethyl]amino]-7-bromo-9-oxothioxanthen-4-carboxaldehyde (II: $R^1=R^2=Et$; $R^8=7$-Br; n=2)

A mixture of 3.2 g (7.34 mmol) of the alcohol of Example 32(d) and 4.3 g of $MnO_2$ in 85 mL of toluene was heated at 60° C. for 1 h under nitrogen. The mixture was filtered, washed with $CHCl_3$, and the combined filtrate was concentrated in vacuo affording 3 g of a yellow solid. The yellow solid was triturated in ether, filtered, and dried to afford 2.7 g (94.3%) of 1-[[2-(diethylamino)ethyl]amino]-7-bromo-9-oxothioxanthen-4-carboxaldehyde, m.p. 145°–146° C.

(f)

N-[[1-[[2 - (Diethylamino) ethyl]amino]-7-bromo-9-oxothioxanthen-4-yl]methyl]formamide (I: $R^1=R^2=Et$; $Q=CH_2NHCHO$; $R^8=7$-Br; n=2)

A mixture of 2.7 g (6.2 mmol) of 1-[[2-(diethylamino)ethyl]amino]-7-bromo-9-oxothioxanthen-4-carboxaldehyde, 31.7 mL of formamide, and 3.6 mL of formic acid was heated to 170° C. under nitrogen and with stirring for 8 h and the mixture was allowed to stand at room temperature for 72 h. The mixture was poured into 150 mL of ice/water, basified with 35% NaOH solution, and the solid product was filtered and washed with water. The solid product was dissolved in chloroform, washed with brine, dried over sodium sulfate, and the solvent was concentrated in vacuo to afford 2.85 g of the desired formamide, as a yellow/orange solid, m.p. 132° C. (dec.).

(g)

1-[[2-(Diethylamino)ethyl]amino]-4-(aminomethyl)-7-bromothioxanthen-9-one (I: $R^1=R^2=Et$; $Q=CH_2NH_2$; $R^8=7$—Br; n=2)

A mixture of 2.85 g (6.6 mmol) of the above formamide (Example 32(f)) in 26 mL of 2N HCl solution was heated to 100° C. under nitrogen for 2h and the mixture was allowed to stand at room temperature overnight. The reaction mixture was poured into 200 mL of ice/water, basified with 35% NaOH solution, and extracted into chloroform. The organic layer was washed with water and brine, dried over sodium sulfate, and concentrated in vacuo to yield 2.67 g of a dark oil. The dark oil was purified by flash chromatography (silica gel; 1250 mL of hexane/chloroform (1:1), and then 1% isopropylamine in hexane/chloroform (1:1)) to afford 1.87 g (70%) of 1-[[2-(diethylamino)ethyl]amino]-4-(aminomethyl)-7-bromothioxanthen-9-one, m.p. 79°–82° C.

EXAMPLE 33

N-[[1-[[2-(Diethylamino)ethyl]amino]-7-bromo-9-oxothioxanthen-4-yl]methyl]methanesulfonamide (I: $R^1=R^2=Et$; $Q=CH_2NHSO_2Me$; $R^8=7$—Br; n=2)

1-[[2-(Diethylamino)ethyl]amino]-4-(aminomethyl)-7-bromothioxanthen-9-one (1 g, 2.3 mmol) in 11.5 mL of dry pyridine under nitrogen was stirred in an ice bath for 15 min and 0.2 mL (2.6 mmol) of methanesulfonyl chloride in chilled pyridine was added dropwise and the mixture was stirred at room temperature. The reaction mixture was poured into 200 mL of water, added 0.19 g of sodium hydroxide in ice/water, and extracted into chloroform. The organic layer was washed with water (2x) and brine, and dried over anhydrous sodium sulfate. The mixture was filtered, concentrated in vacuo and the residue was stirred in ether, filtered, and dried to afford 1.02g of N-[[1-[[2-(diethylamino)ethyl]amino]-7-bromo -9-oxothioxanthen-4-yl]methyl]-methanesulfonamide, m.p. 134°–139° C.

EXAMPLE 34

Methyl N-[[1-[[2-(diethylamino)ethyl]amino]-9-oxothioxanthen-4-yl]methyl]carbamate (I: $R^1=R^2=Et$; $Q=CH_2NHCOOMe$; $R^8=H$; n=2)

To a solution of 2.94 g (8.27 mmol) of 4-(aminomethyl)-1-[[2-(diethylamino)]ethyl]amino]-thioxanthen-9-one in 50 mL of methylene chloride containing 5 mL of triethylamine chilled to 0° C. was added 0.7 mL (9.06 mmol) of methyl chloroformate and the mixture was stirred for 2.5 h. The solvent was removed in vacuo, the residue was suspended in chloroform and was purified by flash chromatography (silica gel; chloroform, then 1% isopropylamine/chloroform) affording 2.36 g (69%) of methyl N-[[1-[[2-(diethylamino) ethyl]amino]-9-oxothioxanthen-4-yl]methyl]-carbamate, as a yellow solid, m.p. 129°–131° C.

EXAMPLE 35

1-[[2-(Diethylamino)ethyl]amino]-4-[(methylamino) methyl]-7-hydroxy-thioxanthen-9-one (I: $R^1=R^2=Et$; $Q=CH_2NHMe$; $R^8=7$—OH; n=2)

A solution of 1.6 g (4 mmol) of 1-[[2-(diethylamino) ethyl]amino]-4-[(methyl-amino]methyl]-7-methoxy-thioxanthen-9-one (prepared by the process described in Example 30(h)) in 10 mL of a 48% HBr solution was heated to 110° C. for 5 h. After cooling, the reaction mixture was neutralized with saturated sodium bicarbonate and extracted into chloroform (3×100ml). A dark gum, insoluble in water or chloroform, was dissolved in methanol and combined with chloroform solution. The solvent was concentrated in vacuo to afford 1.67 g of a dark orange solid. The orange solid product was purified by flash chromatography (silica gel; isopropylamine/methanol/chloroform (1:1:98) followed by a second silica column eluting with isopropylamine/ MeOH/CHCl$_3$ (2:2:96)) affording 0.56 g (36%) of 1-[[2-(diethylamino)ethyl]-amino]-4-[(methylamino]methyl]-7-hydroxy-thioxanthen-9-one, m.p. 167°–169° C.

EXAMPLE 36

Methyl N-[[1-[[2-(diethylamino)]ethyl]amino]-7-methoxy-9-oxothioxanthen-4-yl]-methyl]carbamate (I: $R^1=R^2=Et$; $Q=CH_2NHCOOMe$; $R^8=7$-OMe; n=2)

To a solution of 1.55 g of 4-(aminomethyl)-1-[[2-(diethylamino)ethyl]amino]-7-methoxythioxanthen-9-one in 40 mL of chloroform containing 2 mL of triethylamine chilled to 0° C. was added 0.45 mL of methyl chloroformate and the mixture was stirred at room temperature for several hours. The solvent was removed in vacuo, the residue was purified by flash chromatography (silica gel; eluting with chloroform, then 1% triethylamine in chloroform/hexane (1:1)) affording 1.2 g of methyl N-[[1-[[2-(diethylamino) ethyl]amino]-7-methoxy-9-oxothioxanthen-4-yl]-methyl] carbamate which was recrystallized from ethyl acetate to yield 0.79 g of a bright yellow solid, m.p. 131°–132° C.

EXAMPLE 37

N-[[1-(2-Diethylamino)ethyl]amino]-7-hydroxy-9-oxothioxanthen-4-yl]methyl]methanesulfonamide·¾ hydrate (I: $R^1=R^2=Et$, $Q=CH_2NHSO_2CH_3$; $R^8=7$—OH; n=2)

To a solution of N-[[1-(2-(diethylamino)ethyl]amino]-7-methoxy-9-oxothioxanthen-4-yl]methyl] methanesulfonamide (0.5 g) in CH$_2$Cl$_2$(45 mL) at −78° C. was added in BBr$_3$ in CH$_2$Cl$_2$ (1.75 mL). The mixture was warmed to room temperature, stirred overnight, and then poured into ice-water (250 mL) containing 35% NaOH (8 mL). The mixture was acidified with dilute HCl, then basified with solid Na$_2$CO$_3$ and then was extracted with ethyl acetate. The organic layer was separated, washed with brine, dried over Na$_2$SO$_4$ and concentrated in vacuo. The residue was purified by column chromatography on silica eluting with 5% MeOH/EtOAc to afford 0.28 g (58%) of N-[[1-(2-diethylamino)ethyl]amino]-7-hydroxy-9-oxothioxanthen-4-y]methane-ulfonamide·¾ hydrate, m.p. 78° C. (dec.).

Representative examples of the invention were tested for antitumor activity in mice according to the following procedure:

The animals were pooled, implanted subcutaneously with 30 to 60 mg tumor fragments by 12-gauge trocar, and again pooled before unselective distribution to the various treatment and control groups. For early-stage treatment, chemotherapy was started within 1 to 5 days after tumor implantation while the number of cells was relatively small ($10^7$ to $10^8$ cells). For advanced-stage treatment, chemotherapy was delayed until the tumor became relatively large (200 to 300 mg in size). A 300-mg tumor contains approximately 3×10$^8$ total cells. Tumors within a given advanced-stage trial were within a 2.5-fold size range for 90% of the animals. Tumors were measured with a caliper weekly (or twice weekly for the more rapidly growing tumors). Mice were sacrificed when their tumors reached 1500 mg (i.e., before they can cause the animal discomfort). Tumor weights were estimated from two-dimensional measurements.

The treatment and control groups were measured when the control group tumors reached approximately 700 to 1200 mg in size (Median of Group). The median tumor weight of each group was determined (including zeros). The T/C value (weight of treated tumors over the weight of control tumors) in percent is an indication of antitumor effectiveness: A T/C equal to or less than 42% is considered significant antitumor activity by the Drug Evaluation Branch of the Division of Cancer Treatment (NCI). A T/C value <10% is considered to indicate highly significant antitumor activity. A body weight loss nadir (mean of group) of greater than 20% or greater than 20% drug-deaths is considered to indicate an excessively toxic dosage.

The results are shown in Table I for pancreatic ductal adenocarcinoma #03 and in Table 2 for colon adenocarcinoma #38.

TABLE 1

| Example # | T/C (%) | Weight Loss (g)* | Drug Deaths | Total Dose (mg/kg) i.v. or p.o. |
|---|---|---|---|---|
| 1 | 0 | 1.6 | 0 | 1739 |
| 2 | 0 | 2.0 | 0 | 576 |
| 2 | 7 | 1.6 | 0 | 144 |
| 4 | 0 | 0.4 | 0 | 570 |
| 5 | 0 | 1.6 | 0 | 222 |
| 6 | 0 | 1.6 | 0 | 124 |
| 7 | 0 | 3.2 | 1/5 | 400 |
| 8 | 0 | 0.8 | 0 | 304 |
| 9 | 8 | 1.6 | 0 | 1395 |
| 10 | 0 | 2.4 | 0 | 540 |
| 11 | 0 | 0.8 | 0 | 855 |
| 12 | 36 | 3.2 | 0 | 1298 |
| 13 | 0 | 2.4 | 0 | 431 |
| 14 | 0 | 1.2 | 0 | 448 |
| 15 | 0 | 2.0 | 0 | 390 |
| 16(a) | 21 | +0.8 | 0 | 1171 |
| 17(f) | 17 | 2.0 | 0 | 1060 |
| 18(e) | 82 | 1.0 | 0 | 128 |
| 18(f) | 0 | 5.2 | 2/5 | 256 |
| 19(e) | 4 | 3.4 | 0 | 610 |
| 20(b) | 10 | 0.4 | 0 | 383 |
| 21(c) | 0 | 4.5 | 0 | 208 |
| 22 | 0 | 3.2 | 0 | 465 |
| 23 | 20 | 2.4 | 0 | 1212 |
| 24 | 0 | 2.3 | 0 | 203 |
| 25 | 0 | 4.6 | 0 | 288 |
| 26 | 13 | 2.2 | 0 | 654 |
| 27 | 5 | +0.8 | 0 | 2594 |
| 28 | 0 | 2.8 | 0 | 552 |
| 29 | 6 | 2.4 | 0 | 2403 |
| 31(c) | 0 | 5.6 | 0 | 248 |
| 30(h) | 0 | 1.4 | 0 | 880 |
| 33 | 28 | 2.0 | 0 | 1281 |
| 34 | 0 | 3.6 | 0 | 248 |
| 36 | 0 | 0.4 | 0 | 155 |
| 37 | 7 | 0 | 0 | 32 |

*Average body weight was 25 g.

TABLE 2

| Example # | T/C (%) | Weight Loss (g)* | Drug Deaths | Total Dose (mg/kg) i.v. |
|---|---|---|---|---|
| 2 | 0 | 2.8 | 0 | 600 |
| 5 | 11 | 2.9 | 0 | 960 |
| 6 | 0 | 5.0 | 3/7 | 132 |
| 6 | 4 | 1.7 | 1/7 | 82 |
| 7 | 16 | 0.6 | 0 | 840 |
| 10 | 0 | 4.0 | 0 | 340(b) |
|  | 24 | 2.3 | 0 | 200(b) |
|  | 22 | 0.6 | 0 | 160(b) |
|  | 2 | 4.0 | 2/5 | 740(a) |
|  | 7 | 1.2 | 0 | 460(a) |
|  | 23 | 2.0 | 0 | 865(b) |
| 11 | 0 | 2.0 | 0 | 1709(a) |
|  | 0 | 0.8 | 0 | 885(a) |
|  | 39 | 0.8 | 0 | 518(b) |
| 16(a) | 20 | 1.2 | 0 | 1000 |
|  | 27 | 1.5 | 0 | 690 |
| 18(e) | 51 | 2.2 | 4/5 | 180 |
|  | 3 | 1.0 | 0 | 120 |
| 25 | 0 | 4.8 | 4/5 | 852(c) |
|  | 0 | 0.6 | 0 | 529(c) |
|  | 0 | 0.8 | 0 | 327(c) |

*Average body weight was 20.5–25.5 g.
(a) = p.o. administration.
(b) = i.p. administration.
(c) = i.v. administration days 3–6 and p.o. administration days 7–10

The compound of Example 5 was tested by intravenous infusion against a number of other tumors as shown in Table 3, and was active at 300 mg/kg p.o. against colon adenocarcinoma #38.

The compound of Example 6 was tested by bolus intravenous injection against a number of other tumors as shown in Table 4.

The compound of Example 8(a) was tested against a number of tumors as shown in Table 5.

The compound of Example 36 was tested against a number of tumors as shown in Table 6.

Representative compounds of the invention were tested against Mammary Adenocarcinoma 16/C/RP as shown in Table 7.

Representative compounds of the invention were tested against P388/adriamycin resistant leukemia as shown in Table 8.

TABLE 3

| Tumor | Total Dosage mg/kg | Schedule | Wt. Loss at Nadir g/mouse | T/C Value in % | Tumor Free | Days of Observation |
|---|---|---|---|---|---|---|
| Human Adeno Squamous Lung #125 | 960 | 16 hr infusion days 7, 20 | −0.4 | 16% | 1/4 | 33 |
|  |  |  | −0.4 | 16% | 0/4 | 132 |
|  | 600 |  | −0.4 | 15% | 0/5 | 33 |
|  |  |  | −0.4 | 15% | 0/5 | 132 |
| Mammary 16/C | 720 | 4 hr infusion days 1, 4 | −2.0 | 18% | 0/7 | 13 |
|  | 454 |  | −1.2 | 16% | 0/7 | 13 |
| Mammary 16/C/Adr* | 960 | 3 hr infusion days 1, 4 | −2.8 | 23% | 0/7 | 27 |
| Colon Adenocarcinoma #38 | 732 | 3–15 bolus | −2.0 | 0% | 1/5 | 100 |
|  | 477 |  | −2.8 | 9% | 0/5 | 100 |
| Colon Adenocarcinoma #38 | 960 | 4 hr infusion days 6, 13 | −2.9 | 11% | 2/7 | 20 |
|  |  |  | −2.9 | 11% | 1/7 | 100 |
|  | 600 |  | −2.0 | 26% | 0/7 | 20 |
|  |  |  | −2.0 | 26% | 0/7 | 100 |

TABLE 3-continued

| Tumor | Total Dosage mg/kg | Schedule | Wt. Loss at Nadir g/mouse | T/C Value in % | Tumor Free | Days of Observation |
|---|---|---|---|---|---|---|
| Colon #51 | 720 | 3 hr infusion | −1.1 | 8% | 0/5 | 50 |
|  | 454 | days 3, 7 | −2.8 | 12% | 0/7 | 50 |
| Panc 03 | 222 | 3 hr infusion | −1.6 | 0 | 1/4 | 108 |

*adriamycin resistant

TABLE 4

| Tumor | Total Dosage mg/kg | Schedule | Wt. Loss at Nadir g/mouse | T/C Value in % | Tumor Free | Days of Observation |
|---|---|---|---|---|---|---|
| Colon Adenocarcinoma #38 | 82 | days 6–9 | −1.7 | 1 | 2/7 | 132 |
|  | 51 | bolus | −1.2 | 18 | 1/7 | 132 |
| Mamary 16/C | 82 | days 1–4 | −3.0 | 6 | 0/5 | 23 |
|  | 51 | bolus | −1.2 | 13 | 0/5 | 23 |
| Colon 51/A | 96 | days 3–6, 9, 11 | −3.0 | 14 | 0/6 | 32 |
|  | 66 | bolus | −2.3 | 28 | 0/6 | 32 |
| Panc 02 | 82 | days 1–4 | −2.0 | 23 | 0/5 | 28 |
|  | 51 | bolus | −1.2 | 42 | 0/5 | 28 |
| Panc 03 | 124 | days 3–4, 6–14 | −1.6 | 0 | 3/5 | 245 |
|  | 79 | bolus | −1.0 | 0 | 1/5 | 245 |

TABLE 5

| Tumor | Total Dosage mg/kg | Drug Route | Schedule | Wt. Loss at Nadir g/mouse | T/C Value in % | Drug Deaths | Tumor Free | (Days of Observation) |
|---|---|---|---|---|---|---|---|---|
| Colon Adenocarcinoma #38 | 340 | i.p. | days 3–10 | −2.0 | 0 | 0 | 5/5 | 168 |
|  | 196 | i.p. | days 3–10 | −0.0 | 0 | 0 | 1/5 | 168 |
|  | 112 | i.p. | days 3–10 | +0.4 | 3 | 0 | — — | 168 |
|  | 550 | p.o. | days 3–7 | −2.8 | 0 | 0 | 5/5 | 168 |
|  | 275 | p.o. | days 3–7 | −0.4 | 0 | 0 | 3/5 | 168 |
| Colon 51/A | 500 | p.o. | days 3–7 | −4.6 | 0 | 4/5 | 0/5 | 31 |
|  | 250 | p.o. | days 3–7 | −1.6 | 16 | 0 | 0/5 | 31 |
| Mammary 16/C/Adr* | 340 | i.v.→p.o. | i.v. 2X/day days 1–4; p.o. day 5 | −7.1 | 32 | 5/6 | 0/6 | 22 |
|  | 284 | i.v.→p.o. | i.v. 2X/day days 1–4; p.o. days 5–6 | −2.3 | 61 | 3/6 | 0/6 | 22 |
|  | 183 | i.v.→p.o. | i.v. 2X/day days 1–4; p.o. days 5–6 | −4.3 | 39 | 0/4 | 0/4 | 22 |

*adriamycin resistant

TABLE 6

| Tumor | Total Dosage mg/kg | Drug Route[a] | Schedule | Wt. Loss at Nadir g/mouse | T/C Value in % | Drug Deaths | Tumor Free | Days of Observation |
|---|---|---|---|---|---|---|---|---|
| Panc 03 | 420 | i.v. | days 3–6 | −5.6 | 0 | 3/5 | 2/5 | 45 |
|  | 240 | i.v. | days 3–6 | −0.4 | 0 | 0 | 5/5 | 45 |
|  | 155 | i.v. | days 3–6 | −0.4 | 0 | 0 | 5/5 | 45 |
| Colon Adenocarcinoma #38 | 330 | i.v. | days 3–7 | −3.2 | 0 | 0 | 5/5 | 33 |
|  | 220 | i.v. | days 3–7 | −0.8 | 0 | 0 | 5/5 | 33 |
|  | 147 | i.v. | days 3–7 | 0 | 0 | 0 | 5/5 | 33 |
| Mammary 16/C | 363 | i.v. | days 1–4 | −2.4 | 2 | 2/5 | 2/5 | 21 |

TABLE 6-continued

| Tumor | Total Dosage mg/kg | Drug Route[a] | Schedule | Wt. Loss at Nadir g/mouse | T/C Value in % | Drug Deaths | Tumor Free | Days of Observation |
|---|---|---|---|---|---|---|---|---|
| | 242 | i.v. | days 1–4 | −1.2 | 8 | 1/5 | 0/5 | 21 |
| | 161 | i.v. | days 1–4 | −0.4 | 9 | 0 | 0/5 | 21 |
| Human MX-1 | 297 | i.v. | days 1–6 | −2.4 | 39 | 0 | 0/5 | 26 |
| Mammary | 132 | i.v. | days 1–6 | −0.8 | 27 | 0 | 0/5 | 26 |

[a]Note some injections were changed to p.o. after 2–4 days of injections due to tail vein damage.

TABLE 7

| Example No. | Total Dosage mg/kg | Drug Route | Schedule | Wt. Loss at Nadir g/mouse | T/C Value in % | Drug Deaths | Tumor Free | Days of Observation |
|---|---|---|---|---|---|---|---|---|
| 30(H) | 900 | i.v. infusion | infusion days 1, 4 | 0 | 29 | 1/6 | 0/5 | 63 |
| | 600 | i.v. infusion | infusion days 1, 4 | −0.7 | 23 | 0/5 | 0/5 | 63 |
| | 400 | i.v. infusion | infusion days 1, 4 | −1.0 | 46 | 0/5 | 0/5 | 63 |
| 31(C) | 224 | i.v. | 2X/day, days 3–6 | −4.4 | 0 | 0 | 1/5 | 28 |
| | 156.8 | i.v. | 2X/day, days 3–6 | −1.6 | 5 | 0 | 0/5 | 28 |
| | 109.6 | i.v. | 2X/day, days 3–6 | −1.6 | 6 | 0 | 1/5 | 28 |

TABLE 8

| Example No. | # of P388/Adr cells implanted i.v. on day 0 | Total Dosage mg/kg | Drug Route | Schedule | Wt. Loss at Nadir g/mouse | Drug Deaths | % ILS | $Log_{10}$ Tumor cell kill | Tumor Cell | Days of Observation |
|---|---|---|---|---|---|---|---|---|---|---|
| 10 | $10^5$ | 520 | i.v. 3 hour infusion | days 1, 4 | −3.75 | 3/7 | 54 | 3.5 | 0.7 | 129 |
| | $10^5$ | 320 | i.v. 3 hour infusion | days 1, 4 | −1.75 | 0/5 | 23 | 1.5 | 0/5 | 129 |
| | $10^5$ | 200 | i.v. 3 hour infusion | days 1, 4 | −1.5 | 0/7 | 8 | 0.5 | 0/7 | 129 |
| 13 | $10^5$ | 450 | i.v. 3 hour infusion | days 1, 4 | −3.0 | 2/7 | 38 | 2.5 | 0/7 | 129 |
| | $10^5$ | 300 | i.v. 3 hour infusion | days 1, 4 | −1.75 | 0/7 | 15 | 1.0 | 0/7 | 129 |
| | $10^5$ | 150 | i.v. 3 hour infusion | days 1, 4 | −1.75 | 0/8 | 8 | 0.5 | 0/8 | 129 |
| 30(H) | $10^6$ | 450 | i.v. 3 hour infusion | day 1 | −2.3 | 0/7 | 62 | 5.3 | 0/7 | 43 |
| | $10^6$ | 280 | i.v. 3 hour infusion | day 1 | −1.7 | 0/7 | 69 | 6.0 | 2/7 | 43 |
| 31(C) | $10^6$ | 248 | i.v.→p.o.* | days 1, 4 | −3.0 | 1/6 | 0 | 0 | 0/6 | 43 |
| | $10^6$ | 112 | i.v.→p.o.* | days 1, 4 | −2.7 | 0/6 | 0 | 0 | 0/6 | 43 |
| 34 | $10^6$ | 320 | i.v. 3.5 hour infusion | day 1 | −3.6 | 5/5 | toxic | $LD_{100}$ | 0/5 | 23 |
| | | 198 | i.v. 3.5 hour infusion | day 1 | −1.2 | 0/5 | 41.7 | 3.3 | 0/5 | 23 |
| | | 123 | i.v. 3.5 hour infusion | day 1 | −1.2 | 0/5 | 8.3 | 0.7 | 0/5 | 23 |
| | | 76 | i.v. 3.5 hour infusion | day 1 | −0.4 | 0/5 | 0 | 0 | 0/5 | 23 |

*p.o. injection day 4 due to tail vein damage.
% ILS = the percentage increase in lifespan.

During the conduct of the above-described testing, the investigators have encountered degradation problems with injectable solutions that were not freshly made prior to injection. A project was then undertaken to provide injectable solutions that do not degrade on standing so that the antitumor agents could be used in the medical field for the treatment of tumors in patients.

The compound of Example 6 having the structure

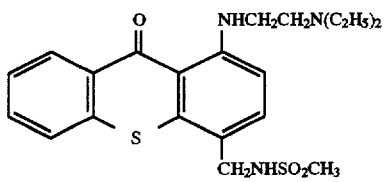

and chemical name N-[[1-[[2-(Dimethylamino)ethyl]amino]-9-oxothioxanthen-4-yl]methyl]methanesulfonamide having cytotoxic antineoplastic activity was used in the project studies. This compound will sometimes be designated hereinafter as WIN 33377 for ease of reference. The compound has been evaluated in clinical studies using a terminally stabilized solution formulation in ampoules at a concentration of 2.5 mg/ml in citrate buffer (pH 5.5). In order to achieve an acceptable shelf like, the formulation was stored under refrigeration (2°–8° C.). Storage at higher temperatures led to the formation of a very sparingly soluble dimeric species which precipitated at a low concentration. A freeze-dried formulation may be required to provide a commercially acceptable product which could be stored at ambient temperature.

Three formulations were employed, as shown in Table 9:

TABLE 9

| Formulation | 1 | 2 | 3 |
| --- | --- | --- | --- |
| WIN 33377 | 10.0 mg | 10.0 mg | 10.0 mg |
| Acetic acid (0.1 M) | 0.5 ml | | |
| Citric acid (0.1 M) | | 9.6 mg | |
| Lactic acid (0.1 M) | | | 0.5 ml |
| Sodium hydroxide (0.5 M) | 8.8 µl | 12 µl | |
| Water for injection to | 1 ml | 1 ml | 1 ml |
| pH | 4.95 | 3.98 | 3.99 |

Aqueous formulations of WIN 33377 were made before additions of stabilizers.

Three stabilizers were added to the solutions at various concentrations: mannitol (Fison AR grade M/2405), dextran (Sigma Chemical Co. Clinical grade D-4751) and sucrose (Prolabo Normapur AR grade 27480.294).

A Perkin-Elmer DSC-II fitted with a subambient temperature accessory was employed. Data were collected and analyzed on a Dell 210 microcomputer with DARES software. Temperature calibration was performed, as described in the manufacturer's manual, with indium and water as reference materials. Liquid samples for analysis were sealed in large stainless steel pans. They were loaded into the calorimeter at 27° C. and submitted to a cool/heat cycle between −53° C. and 27° C. Heating and cooling rates were 5 deg/min. Freeze-dried samples were also sealed into large stainless steel pans, but under a dry nitrogen atmosphere, to reduce the possibility of moisture uptake by the dried cake. A heating and cooling rate of 10 deg/min to enhance the amplitude of any signal was employed over the temperature range −53° C. to 127° C. Freeze-drying was performed in a laboratory freeze-drier.

Stability evaluations of freeze-dried samples were conducted using a High Performance Liquid Chromatographic (HPLC) technique which provided assay of WIN 33377 or of the total chromatographic impurities.

Assay Method

Using HPLC equipment (Kontron), chromatography was conducted under the following conditions:

| | |
| --- | --- |
| Column: | Partisil ODS - 3, 5 µm, 10 × 0.46 cm |
| Mobile phase: | A:B (77:23 v/v) |
| where | A = 0.5 M ammonium acetate buffer, pH 4.8 |
| and | B = acetonitrile |
| Flow rate: | 2.0 ml/min |
| Detecter wavelength | 258 nm |
| Temperature: | 40° C. |
| Injection volume: | 20 µl |

Total Chromatographic Impurities Method

A gradient elution HPLC technique was used for total chromatographic impurity determinations, with the following conditions:

| | | |
| --- | --- | --- |
| Column: | | Hypersil BDS, C18, 5 µm, 25 × 0.46 cm i.d. |
| Mobile phase: | A: | 7.71 g/l ammonium acetate + 6.0 ml/l glacial acetic acid + 10 ml/l triethylamine, adjusted to pH 4.8 |
| | B: | acetonitrile |

Gradient Conditions

| Time(min) | % A | % B |
| --- | --- | --- |
| 0.00 | 80 | 20 |
| 30.00 | 80 | 20 |
| 60.00 | 60 | 40 |
| 70.00 | 60 | 40 |
| 70.01 | 80 | 20 |
| 80.00 | 80 | 20 |
| Flow rate: | | 2.0 ml/min |
| Detector wavelength: | | 438 nm |
| Temperature: | | 40° C. |
| Injection volume: | | 25 µl |

Formulation Development

The first step in any freeze-drying process development is to fully characterize the physiochemical properties of the solutions before formulation for freeze-drying is attempted. Samples of the three formulations, as given in Table 9, were analyzed by DSC according to the procedure described above. The relevant transition temperatures are summarized in Table 10.

TABLE 10

| Formulation | Buffer | Temperature of transition 1(°C.) | Temperature of transition 2(°C.) |
| --- | --- | --- | --- |
| 1 | Acetate | −28 | −17 |
| 2 | Citrate | −33 | −17 |
| 3 | Lactate | −32 | |

The three mixtures were found to display different physiochemical behavior: the acetate-based formulation was found to be crystalline; the citrate-based formulation was found to be part crystalline while the remaining part forms a glass; and the lactate-based formulation forms a glass.

Of these three types of behaviors, partial crystallization presents the greatest problems for freeze-drying. Partial crystallization is usually unpredictable and, in the case of pharmaceuticals produced in vials, can result in significant differences in the frozen product structure between vials. This, in turn, can cause variations in the drying effectiveness between vials. The net result is an intra-batch variation in product quality, such as stability, rehydration and shelf-life, between vials. Moisture content variations between vials are the most immediate indicator of this problem.

Incomplete crystallization, as displayed by the citrate formulation, can be prevented by adding a suitable glass forming excipient to the mixture. This excipient will prevent the crystallization of other material(s) and result in vitrification. The amount of glass former to be added will depend on the nature of the crystallizing material and the crystallization rate. In the present investigation citrate was rejected, mainly on the ground that in the citrate buffer, the drug, although dissolved during the initial preparation, crystallized out during storage at 4° or 25° C. within a few hours. Since freeze-drying does not affect the solubility of the drug, thus, when the citrate formulation is rehydrated at the point of use, some difficulty in dissolution may be encountered and, additionally, sporadic crystallization might even occur during administration.

The overall solute content of all three formulations was low, about 1 to 2% w/w. This level is insufficient to maintain an adequate plug structure; reformulation was therefore needed. Crystalline formulation 1 required the addition of a bulking agent. Formulation 3 (amorphous), on the other hand, required the addition of a glass former. Selected stabilizers were mannitol for the crystalline, and sucrose or dextran for the amorphous preparation. They were added at concentrations of 50 mg/ml to the solutions described in Table 9. Samples of the formulated solutions were then analyzed by DSC.

The DSC measurements have yielded glass transition temperature values for the three preparations. These temperatures represent the maximum permissible primary drying temperatures, if collapse and deterioration are to be minimized. The dextran-containing system has the highest glass transition temperature and will allow, as the sublimation rate of ice increases exponentially with increasing temperature, the shortest drying cycle. However, WIN 33377 requires repeated administration, and dextran may, under such circumstances, cause anaphylactic shock reactions. This formulation was therefore rejected for clinical reasons.

For the other two formulations the following findings were made.

For the sucrose/lactate formulation primary drying should be performed at about –40° C. This allows a safety margin of 5° C. (sufficient for the actual drier employed) to compensate for temperature gradients within the drier. Each vial contained 10 ml of product at an approximate fill depth of 1.63 cm. The diameter of the vial, 2.8 cm, gave a product surface area of 6.15 cm². The effective sublimation rate for these samples was calculated as 0.226 g/vial/h of the total product mass, approximately 9.4 g consisted of ice, the remainder being made up of solids and unfrozen water. At a rate of 0.226 g/h approximately 42 h are required to completely sublime the ice at –40° C.

For the mixed mannitol/acetate formulation the primary drying must be performed below the lowest thermal transition detected by DSC for the acetate formulation, i.e., –30° C. The fill volumes and dimensions of the vials were the same, but the sublimation could now be performed at a higher temperature; the calculated effective sublimation rate for these samples was 0.670 g/vial/h. As before, 9.4 g of ice had to be sublimed; the primary drying time was now reduced to 14 h.

Maintaining the products at the recommended temperatures for the duration outlined above will, subject to the temperature at the sublimation front being equal to that of the ice core, ensure the completion of primary drying. The product temperature must then be increased by a gradual ramping of the shelf temperature, in order to remove the residual moisture in the product.

Preparation of Freeze-Dried Products

Table 11 shows process variables for optional freeze-drying of acetate and lactate-buffered solutions, stabilized, respectively, with mannitol and sucrose.

TABLE 11

| Formulation | Mannitol | Sucrose |
| --- | --- | --- |
| Vial volume (ml) | 20 | 20 |
| Fill Volume (ml) | 10 | 10 |
| Fill Depth (cm) | 1.63 | 1.63 |
| Primary drying temperature (°C.) | –30 | –40 |
| Primary drying time (h) | 14 | 42 |
| Temperature ramp rate during secondary drying deg/h | 4 | 4 |
| Final drying temperature (°C.) | 25 | 25 |
| Pressure during primary drying (mbar) | 0.3 | 0.1 |

Formulations of the present invention are lyophilized using the following process.

Vials of required dimensions are chosen to be filled by a formulation based upon dose requirements. In choosing vials to accommodate a dose, the fill volume should not exceed some fraction of the volume of the vial. For example, a 5 ml fill should not be introduced into less than a 10 ml vial. After filling, the vials are loaded into the drying chamber and placed directly onto the refrigerated shelves which were pre-chilled to 4° C. Thermocouples are placed inside a number of the vials to monitor the temperature of the formulation during the lyophilization process. The vials are then allowed to equilibrate to the temperature of the shelves (4° C.) before lowering the shelves temperatures to –40° C. for the sucrose formulation and –30° C. for the mannitol formulation. Once reaching –40° C. and –30° C., respectively for the sucrose and mannitol formulations, the vials are kept at this temperature for about 2 hours to allow complete freezing of the formulation. (An annealing step is included for the mannitol formulation at this stage.) After this time period the condenser coils are chilled to –60° C. and the vacuum pump is turned on to evacuate the condenser chamber followed by the process of primary and secondary drying. In the primary drying process, the main valve between the condenser and the drying chamber is opened and the drying chamber is evacuated to a pressure of about 100 microns with a nitrogen gas bleed. This portion of the lyophilization cycle (primary drying) requires about 40 to 50 hours. The primary drying process is complete when all of the ice disappears from the frozen matrix. In the secondary drying process, the temperature is raised from –20° C. or –30° C. to 25° C. to remove all the residual moisture that was not removed during the primary drying process. This secondary drying period is required for approximately 15 hours.

After the completion of the secondary drying process the main valve is closed off and the drying chamber is filled with nitrogen so as to maintain a slight vacuum in the chamber. The stoppering ram is then activated and the closures are pushed down into the vials. The drying chamber is then equilibrated to atmospheric pressure and the chamber door is opened to remove the vials and apply the crimp seals. The vials then are stored at the prescribed temperature until reconstituted with water for injection.

Stability Results

The stability of the dried products was evaluated after storage at 30° C., 40° C. and 50° C. for up to 4 weeks. Assays and chromatographic impurities studies were completed on the samples. Results for the mannitol formulation showed no significant change in drug assay after storing the product for 4 weeks at temperatures up to 50° C. Total chromatographic impurities increased from an initial 0.35 to 0.54% w/w at 30° C., 0.49% w/w at 40° C. and 0.56% w/w at 50° C. The moisture content of the product was 2.4% w/w and the cake appearance was satisfactory, i.e., no product collapse was observed. Two of the five vials, however, did not rehydrate to a clear yellow solution. Vials which could be reconstituted to give a clear solution had a lower pH (5.0) than vials which did not give clear solutions (pH 5.6). This pH shift was considered to be due to the evaporation of acetic acid during freeze-drying.

Stability results for the sucrose formulation (with 5% residual moisture) indicate that there was no change in assay or total chromatographic impurities after storage at 30° C. and 40° C. for 4 weeks. Vials stored at 50° C. showed a decrease in assay and an increase in total chromatographic impurities. Some collapse of the freeze-dried cake was observed after two weeks storage at all temperatures.

Stabilities of WIN 33377/mannitol formulation are shown in Table 12, while stabilities of WIN 33377/sucrose formulation are shown in Table 13.

TABLE 12

| Temp | Initial drug % w/w | Initial impurities % w/w | 2 weeks drug % w/w | 2 weeks impurities % w/w % | 4 weeks drug % w/w | 4 weeks impurities % w/w |
|---|---|---|---|---|---|---|
| Room Temp | 101.6 | 0.35 | — | — | — | — |
| 30° C. | — | — | 100.3 | 0.43 | 98.0 | 0.54 |
| 40° C. | — | — | 102.5 | 0.54 | 100.9 | 0.49 |
| 50° C. | — | — | 101.0 | 0.65 | 98.1 | 0.56 |

TABLE 13

| Temp | Initial drug % w/w | Initial impurities % w/w | 2 weeks drug % w/w | 2 weeks impurities % w/w % | 4 weeks drug % w/w | 4 weeks impurities % w/w |
|---|---|---|---|---|---|---|
| Room Temp | 98.4 | 0.35 | — | — | — | — |
| 30° C. | — | — | 98.4 | 0.32 | 96.8 | 0.33 |
| 40° C. | — | — | 98.2 | 0.31 | 98.1 | 0.34 |
| 50° C. | — | — | 96.8 | 0.51 | 95.2 | 0.87 |

The study has identified a suitable freeze-drying formulation (lactate-sucrose), but this can be further optimized and additional end-use requirements incorporated. It was found that the drug concentration in the initial solution could be increased to 20 mg/ml, thus halving the fill volumes and allowing a reduction in the primary drying time. It was also important to balance isotonicity by the addition of sodium chloride. Since the salt will affect the glass transition temperature (Tg'), the revised formulations (Table 14) were examined by DSC. The glass transition temperature measured are given in Table 15.

TABLE 14

Test formulations used to determine the relative effects of NaCl and sucrose on buffered WIN 33377 solution

| Formulation | A | B | C | D |
|---|---|---|---|---|
| WIN 33377 | 20.0 mg | 20.0 mg | 20.0 mg | 20.0 mg |
| Lactic acid (0.1 M) | 0.5 ml | 0.5 ml | 0.5 ml | 0.5 ml |
| Sodium hydroxide (0.5 M) | 12 µl | 12 µl | 12 µl | 12 µl |
| Sucrose | 100 mg | 50 mg | 40 mg | 30 mg |
| NaCl | 2.7 mg | 2.7 mg | 3.8 mg | 5.0 mg |
| Water for injection to | 1 ml | 1 ml | 1 ml | 1 ml |
| pH | 3.99 | 3.99 | 3.99 | 3.99 |

TABLE 15

Glass transition temperature values measured for the formulations shown in TABLE 14.

| Formulation | Tg'(°C.) |
|---|---|
| Control formulation A without NaCl | −35 |
| A | −37 |
| B | −38 |
| C | −42.5 |
| D | −45.5 |

As shown, the addition of NaCl reduces the glass temperature of the freeze-concentrate. NaCl has a glass transition temperature that is much lower than that of sucrose (−87° C. compared to −32° C.). Thus, as the weight fraction NaCl increases (A through to D), then the glass transition temperature falls towards the value for pure NaCl. The addition of NaCl to the standard 5% sucrose formulation causes a reduction in glass transition temperature of 2° C. Reduction of the sucrose level and a compensatory increase in the NaCl concentration which is necessary to maintain isotonicity, causes further reduction in glass transition temperature. The glass transition temperature of the dried product can be considered to be the maximum temperature to which the product should be exposed. Exceeding the glass temperature will result in the eventual collapse of the plug, rendering the product fluid, in which state diffusion rates rapidly increase, leading to the degradation of the active material. Glass transition temperature depends on moisture content; thus any variance of moisture content within a batch will cause a variance in glass transition temperature. Thus, it is prudent to store the product at least 5° C. below the measured glass temperature, to allow for the variation in the maximum safe storage temperature within a batch.

Formulation Containing WIN 33377 Solution (100 mg) and Sucrose in 20 mL Vial

| Excipient | Amount (mg per vial) |
|---|---|
| WIN 33377 | 100.0 |
| Sucrose | 250.0 |
| Sodium chloride | 5.0 |
| 0.5 M lactic acid solution | 1.0 mL |
| 1.0 M sodium hydroxide | 57.0 µL |
| Water for injections to | 5.0 mL |
| pH (range 3.70–4.30) | 4.00 |

The stability of the preferred sucrose formulation was evaluated during storage at 30° C. and 40° C. for up to 6 months. The assay results and pH are presented in Table 16. The product had an initial moisture content of 1.3% w/w.

Product collapse was observed after 2 weeks storage at 40° C. This was expected since this storage temperature was close to the glass transition temperature for this batch (42° C.). The stability results indicate that the product is chemically stable. i.e., no changes in assay or pH were observed after 6 months storage at 30° C. or 40° C.

TABLE 16

| Time | Temp (°C.) | WIN 33377 (% w/v) duplicate analysis | pH |
|---|---|---|---|
| Initial | Room | 90.85, 90.95 | 3.95 |
| 3 weeks | 30° C. | 89.13, 89.28 | 3.96 |
|  | 40° C. | 90.14, 89.79 | 3.94 |
| 2 months | 30° C. | 90.81, 92.36 | 3.95 |
|  | 40° C. | 88.59, 89.49 | 3.95 |
| 4 months | 30° C. | 93.88, 91.93 | 3.99 |
|  | 40° C. | 95.52, 95.2 | 4.00 |
| 6 months | 30° C. | 90.08, 8-7.68 | 4.02 |
|  | 40° C. | 88.40, 86.75 | 4.05 |

The enhanced stability afforded by the present invention permits storage of the product at room temperatures and increases its shelf-life. This lyophilized product is suitable for packaging in either a convention glass vial or in a prefilled syringe. The formulations have great utility in the treatment of tumors heretofore not provided.

What is claimed is:

1. A reconstituted lyophilized formulation for the treatment of mammalian tumors comprising:

a) of from about 1 to about 50 mg/ml of an antitumor agent having the formula

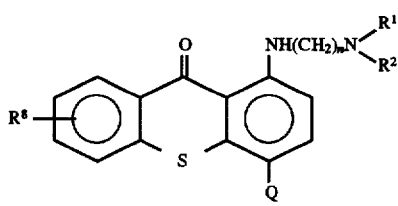

wherein n is 2 or 3;

$R^1$ and $R^2$ are independently lower-alkyl;

Q is a residue chosen from the group consisting of $CH_2NHR^3$, $CH_2N$ $(R^4)$ $SO_2R^7$, $CH_2NHCHO$, $CH=N$—Ar, $C(O)$ $NR^5R^6$, $CH_2N(R^4)$ $C(O)R^7$, $CH_2N$ $(C_2H_5)$ CHO, $CH_2N(R^4)P(O)(O$-lower-alkyl$)_2$, $CH_2N=CH$—N $(R^9)(R^{10})$, $CH_2N$ $(R^4)C(O)CF_3$ and $CH_2N$ $(R^4)$ C (O) $OR^7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy;

Ar is phenyl or phenyl substituted with methyl, methoxyl, hydroxy, halogen or nitro, with the proviso that when n is 2, $R^1$ and $R^2$ are ethyl, $R^8$ is hydrogen and Q is $CH_2NHSO_2Ar$, the Ar group cannot be 4-monosubstituted by methyl or halogen; and $R^9$ and $R^{10}$ are independently lower-alkyl; or a pharmaceutically acceptable acid-addition salt or solvate thereof;

b) of from about 10 to about 125 mg/ml of a stabilizer selected from the group consisting of mannitol and sucrose; and c) of from about 0.025 to about 0.25M of a lactate buffer, said formulation having a pH of from about 3.0 to about 4.5.

2. The reconstituted lyophilized formulation of claim 1 further comprising of from about 1.0 to about 10.0 mg/ml of sodium chloride.

3. The reconstituted lyophilized formulation of claim 1 wherein said lactate buffer is sodium lactate.

4. A reconstituted lyophilized formulation for the treatment of mammalian tumors comprising:

a) from about 1 to about 20 mg/ml of an antitumor agent having the formula

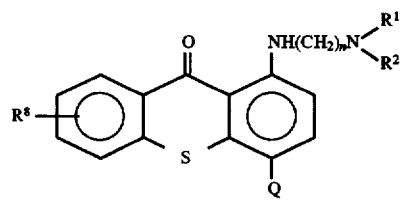

wherein n is 2 or 3;

$R^1$ and $R^2$ are independently lower-alkyl;

Q is a residue chosen from the group consisting of $CH_2NHR^3$, $CH_2NHCHO$, $CH=N$—Ar, $C(O)NR^5R^6$, $CH_2N(R^4)C(O)R^7$, $CH_2N(C_2H_5)CHO$, $CH_2N(R^4)P(O)$ $(O$-lower-alkyl$)_2$, $CH_2N=CH$—$N(R^9)$ $(R^{10})$, $CH_2N$ $(R^4)C(O)CF_3$ and $CH_2N(R^4)C(O)$ $OR_7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy;

Ar is phenyl or phenyl substituted with methyl, methoxyl, hydroxy, halogen or nitro, and $R^9$ and $R^{10}$ are independently lower-alkyl; or a pharmaceutically acceptable acid-addition salt or solvate thereof;

b) of from about 30 to about 100 mg of a stabilizer selected from the group consisting of mannitol and sucrose;

c) of from about 0.025 to about 0.25M of a lactate buffer, said formulation having a pH of from about 3.5 to 4.5.

5. The reconstituted lyophilized formulation of claim 4 further comprising of from about 1.0 to about 10.0 mg/ml of sodium chloride.

6. The reconstituted lyophilized formulation of claim 4 wherein said lactate buffer is sodium lactate.

7. A reconstituted lyophilized formulation for the treatment of mammalian tumors comprising:

a) 1–50 mg of N-[[1-[[2-(di-methylamino)ethyl]amino]-9-oxothioxanthene-4-yl]methyl]methanesulfonamide;

b) 0.025 to about 0.25M of sodium lactate buffer;

c) of from about 10 to 125 mg of sucrose;

d) of from about 1.0 to about 10 mg sodium chloride; and e) water to 1.0 ml, said formulation having a pH of from about 3.0 to about 4.5.

8. A method for treating a susceptible tumor in a mammal which comprises administering to said mammal an amount of the formulation of claim 1 effective to reduce the size of said tumor.

9. A method for treating a susceptible tumor in a mammal which comprises administering to said mammal an amount of the formulation of claim 4 effective to reduce the size of said tumor.

10. A method for treating a susceptible tumor in a mammal which comprises administering to said mammal an amount of the formulation of claim 7 effective to reduce the size of said tumor.

* * * * *